(12) United States Patent
Restifo et al.

(10) Patent No.: US 8,785,149 B2
(45) Date of Patent: Jul. 22, 2014

(54) IN VITRO CELLULAR BIOASSAY FOR NEUROTOXICITY TESTING

(75) Inventors: Linda L. Restifo, Tucson, AZ (US); Robert Kraft, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 13/639,541

(22) PCT Filed: Apr. 8, 2011

(86) PCT No.: PCT/US2011/031774
§ 371 (c)(1),
(2), (4) Date: Apr. 19, 2013

(87) PCT Pub. No.: WO2011/127398
PCT Pub. Date: Oct. 13, 2011

(65) Prior Publication Data
US 2013/0210062 A1 Aug. 15, 2013

Related U.S. Application Data

(60) Provisional application No. 61/342,026, filed on Apr. 8, 2010.

(51) Int. Cl.
C12Q 1/18 (2006.01)

(52) U.S. Cl.
USPC .......................................... 435/32

(58) Field of Classification Search
USPC .......................................... 435/32
See application file for complete search history.

(56) References Cited

PUBLICATIONS

Kraft, R., et al. "Phenotypes of *Drosophila* brain neurons in primary culture reveal a role for fascin in neurite shape and trajectory." J Neurosci. Aug. 23, 2006;26(34):8734-47.
Xiang, Z., et al. "Simvastatin induces cell death in a mouse cerebellar slice culture (CSC) model of developmental myelination." Exp Neurol. Jan. 2009;215(1):41-7. Epub Sep. 27, 2008.
Rand, M.D. "Drosophotoxicology: the growing potential for *Drosophila* in neurotoxicology." Neurotoxicol Teratol. Jan.-Feb. 2010;32(1):74-83. Epub Jun. 24, 2009.
Kraft, R., et al. "The steroid hormone 20-hydroxyecdysone enhances neurite growth of *Drosophila* mushroom body neurons isolated during metamorphosis." J Neurosci. Nov. 1, 1998;18(21):8886-99.

*Primary Examiner* — Ralph Gitomer
(74) *Attorney, Agent, or Firm* — Dann, Dorfman, Herrell & Skillman; Robert C. Netter, Jr.

(57) ABSTRACT

The present invention provides neurotoxicity and developmental neurotoxicity screening methods employing primary cultured neurons from *Drosophila*.

17 Claims, 12 Drawing Sheets

Figure 1:
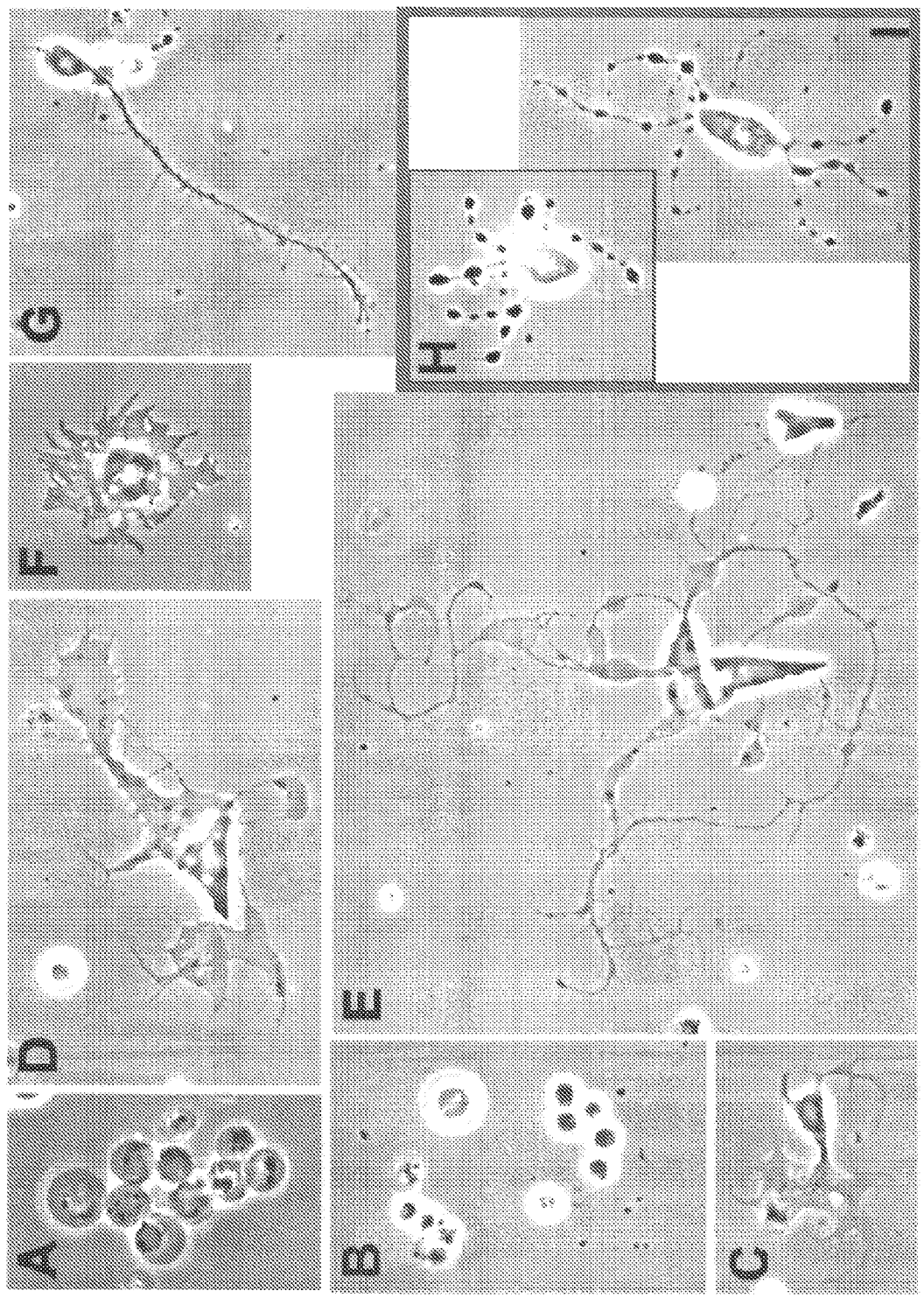

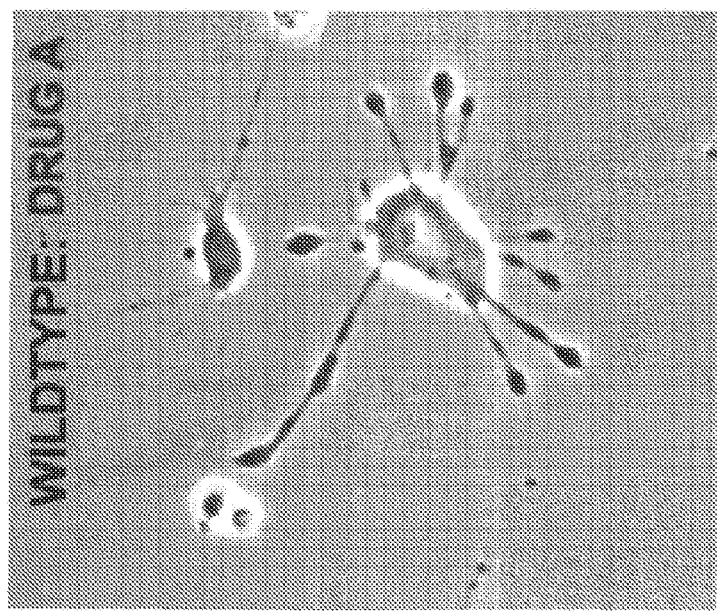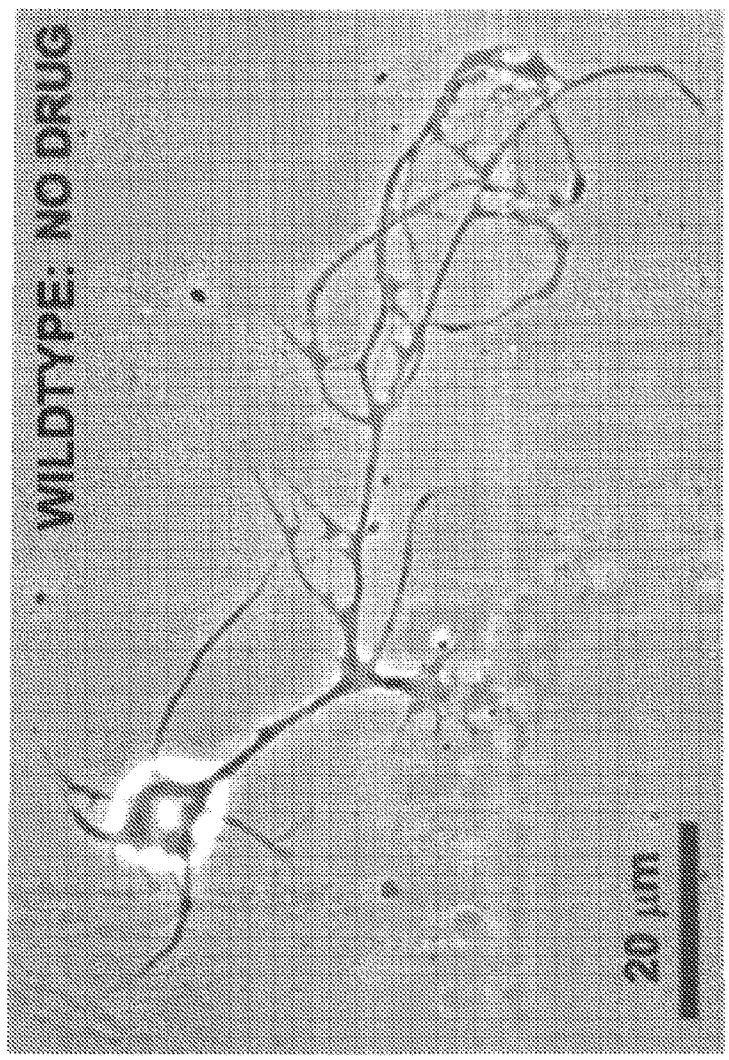
Figure 3

| Compound Name | Neurotoxic Effect |||||||||||||||||||
|---|---|---|---|---|---|---|---|---|---|---|---|---|---|---|---|---|---|---|---|
| | Apparent Cell Death ||||| Altered Neurite Morphology ||||| Altered Cell Body Shape |||| Reduced Neurite Outgrowth |||||
| | 1 | 2 | 3 | 4 | 5 | 6 | 7 | 8 | 9 | 10 | 11 | 12 | 13 | 14 | 15 | 16 | 17 | 18 | 19 |
| 2-MERCAPTOBENZOTHIAZOLE | | X | | | | | | | | | | | | | | | | | |
| 3,3'-DIINDOLYLMETHANE | | X | | | | | | | | | | | | | | | | | |
| 4'-DEMETHYLEPIPODOPHYLLOTOXIN | | | | | | | | | | | | | | X | | X | | X | |
| ACETYCHOLINE | | | | | | | | | | | | | | | | X | | | |
| ACRIFLAVINIUM HCl | X | | | | | | | | | | | | | | | | | | |
| ACRISORCIN | | | X | | | | | | | | | | | | | | | | |
| AKLAVINE HYDROCHLORIDE | | | X | | | | | | | | | | | | | | | | |
| ALMOTRIPTAN | | | | | | | | | | | | | | | X | | | | |
| AMLODIPINE BESYLATE | | | | | | | | | X | | X | | | | | X | | | |
| AMODIAQUINE (HCl)2 | | | | | | | | | | | | | | | | X | | | |
| ANISOMYCIN | | X | | | | | | | | | | | | | | | | | |
| APIGENIN | | | | | | | | | | | | | | | | X | | | |
| APOMORPHINE HCl | | X | | | | | | | | | | | | | X | | | | |
| ASTEMIZOLE | | | | X | | | | | | | | | | | | | | | |
| ATORVASTATIN CALCIUM | | | | | | | | X | | | | | | | | | X | | |
| ATOVAQUONE | | | X | | | | | | | | | | | | | | | | |
| AZADIRACHTIN | | | | | | | X | | | | | | | | | X | | | |
| BACLOFEN | | | | | | | | | | | | | | | X | | | | |
| BENSERAZIDE HCl | | | | | | | | | | | | | | | X | | | | |
| BENZALKONIUM CHLORIDE | | | | X | | X | X | | | | | | | | X | | | | |
| BENZYL ISOTHIOCYANATE | | | | | | | | | | | | | | | | X | | | |
| beta-CAROTENE | | | | | | | | | | | | | | | X | | | | |
| beta-PELTATIN | | X | | | | | | | | | | | | | | | | | |
| BIFONAZOLE | | | X | | | | | | | | | | | | | | | | |
| BITHIONOL | | | | | | | | | | | | | | | | | X | | |
| BROXYQUINOLINE | X | | | | | | | | | | | | | | | | | | |
| CAFFEINE | | | | | | | | | | | | | | | | | | | X |
| CANDESARTAN CILEXTIL | | | X | | | | | | | | | | | | | | | | |
| CARVEDILOL TARTRATE | | | | | | | | | | | | | | | X | | | | |
| CEFAZOLIN SODIUM | | | | | | | | | | | | | | | X | | | | |
| CEFDITOREN PIVOXIL | | | | | | | | | | | | | | | | | X | | |
| CELASTROL | | | X | | | | | | | | | | | | | | | | |
| CEPHALOTHIN SODIUM | | | | | | | | | | | | | | | X | | | | |
| CEPHARANTHINE | | | | | | | | | | | | | | X | X | | | | |
| CETRIMONIUM BROMIDE | | | | X | | | | | | | | | | | X | | | | |
| CETYLPYRIDINIUM Cl | | | | X | | | | | | | | | | | | X | | | |
| CHLORANIL | | | | | | | | | | | | | | | X | | | | |
| CHLORMADINONE ACETATE | | | | | | | | | | | | | | | X | | | | |
| CHLOROACETOXYQUINOLINE | | | X | | | | | | | | | | | | X | | | | |
| CHLOROQUINE DIPHOSPHATE | | | | | | | | | | | | | | | | X | X | | |
| CHLORPROMAZINE | | | | | | | | | | | | | | | | X | | | |
| CICLOPYROX | | | | | | | | | X | | | | | | | | | | |
| CITRININ | | | | | | | | | | | | | | | X | | | | |
| CLINDAMYCINE HCl | | | | | | | | | | | | | | | X | | | | |
| CLOXYQUIN | | | | | X | | | | | | | | | | | X | | | |
| COLCHICEINE | | | | | | | | | | | | | X | | | | | X | |
| COLCHICINE | | | | | | | | | | | | | X | | | | | X | |
| CONVALLATOXIN | | X | | | | | | | | | | | | | | | | | |
| CURCUMIN | | X | | | | | | | | | | | | | | X | | | |
| CYCLOHEXIMIDE | | X | | | | | | | | | | | | | | | | | |
| DEGUELIN | | | X | | | | | | | | | | | | | X | | | |
| DEQUALINIUM CHLORIDE | | | X | | | | | | | | | | | | | | | | |
| DIETHYLSTILBESTROL | | | | | | | | | | | | | | | | | | X | |
| DIETHYLTOLUAMIDE | | | X | | | | | | | | | | | | | | | | |
| DIGITOXIN | | X | | | | | | | | | | | | | | | | | |
| DIGOXIN | | X | | | | | | | | | | | | | | | | | |
| DISULFIRAM | X | | | | | | | | | | | | | | | | | | |
| DYCLONINE HCl | | | | | | | | | | | X | | | | | X | | | |
| ELLAGIC ACID | X | | | | | | | | | | | | | | | | | | |
| EMETINE | | | | | | | | | | | | | | | | X | | | |
| EZETIMIBE | | | | | | | | | | | | | | | X | | | | |
| GAMBOGIC ACID | | | | X | | | | | | | | | | | | | | | |
| GEDUNIN | | X | | | | | | | | | | | | | | X | | | |
| GENTIAN VIOLET | | X | | | | | | | | | | | | | | | | | |
| GINKGOLIC ACID | | | | | | | | | | | | | | X | | X | | | |
| GOSSYPOL | | X | | | | | | | | | | | | | | | | | |
| HEXACHLOROPHENE | | X | | | | | | | | | | | | | | | | | |

Figure 8A

| Compound Name | Neurotoxic Effect | | | | | | | | | | | | | | | | | | |
|---|---|---|---|---|---|---|---|---|---|---|---|---|---|---|---|---|---|---|---|
| | Apparent Cell Death | | | | | Altered Neurite Morphology | | | | | Altered Cell Body Shape | | | | Reduced Neurite Outgrowth | | | | |
| | 1 | 2 | 3 | 4 | 5 | 6 | 7 | 8 | 9 | 10 | 11 | 12 | 13 | 14 | 15 | 16 | 17 | 18 | 19 |
| HEXESTROL | x | | | | | | | | | | | | | | | | | | |
| HEXETIDINE | x | | | | | | | | | | | | | | | | | | |
| HYDROQUINONE | | | x | | | | | | | | | | | | | | | | |
| HYDROXYTACRINE MALEATE | | | | | | | | | | | | | | | | | x | | |
| IOPANIC ACID | | | | | | | | | | | | x | | | | | | | |
| ISORESERPINE | | | | | | | | | | | | | | | | x | | | |
| JUGLONE | | x | | | | | | | | | | | | | | | x | | |
| KITOTIFEN FUMARATE | | x | | | | | | | | | | | | | | | | | |
| L-PHENYLALANINOL | | | | | | | | | | | | | | | | x | | | |
| LANSOPRAZOLE | | x | | | | | | | | | | | | | | | | | |
| LASALOCID SODIUM | | x | | | | | | | | | | | | | | | x | | |
| LEVODOPA | | | | x | | | | | | | | | | | x | | | | |
| LOVASTATIN | | | | | | | | | x | | | | | | | x | | | |
| MENADIONE | x | | | | | | | | | | | | | | | | | | |
| MERBROMIN | x | | | | | | | | | | | | | | | | | | |
| METHYLBENZETHONIUM Cl | | x | | | | | | | | | | | | | | | | | |
| MICONAZOLE NITRATE | | | x | | | | | | | | | | | | | | | | |
| MITOXANTHRONE HCl | | | x | | | | | | | | | | | | | | | | |
| MONENSIN SODIUM | | x | | | | | | | | | | | | | | | | | |
| N-FORMYLMETHIONYLPHENYLALANINE | | x | | | | | | | | | | | | | | | | | |
| NARASIN | | | | x | | | | | | | | | | | | | | | |
| NATEGLINIDE | | | | | | | | | | | | | | x | | | | | |
| NIGERICIN SODIUM | | | | x | | | | | | | | | | | | | | | |
| OUABAIN | x | | | | | | | | | | | | | | | | | | |
| OXAPROZIN | | | | | | | | | | | | | x | | | | | | |
| OXCARBAZEPINE | | | | | | | | | | | | | | | | x | | | |
| OXICONAZOLE NITRATE | | x | | | | | | | | | | | | | x | | | | |
| OXYPHENBUTAZONE | | x | | | | | | | | | | | | | | | | | |
| OXYQUINOLINE HEMISULFATE | | x | | | | | | | | | | | | | | | | | |
| PACLITAXEL | | | | | | | | | | | | | | | | | x | | |
| PATULIN | | x | | | | | | | | | | | | | | | | | |
| PERUVOSIDE | | x | | | | | | | | | | | | | | | | | |
| PHENYLMERCURIC ACETATE | x | | | | | | | | | | | | | | | | | | |
| PICROPODOPHYLLOTOXIN | | | | | | | | | | | | | | | | | | x | |
| PODOFILOX | | | x | | | | | | | | | | | | | x | | | |
| POMIFERIN | | | x | | | | | | | | | | | | | x | | | |
| PRAVASTATIN SODIUM | | | | | | | | | x | | | | | | | x | | | |
| PRIDINOL METHANESULFONATE | | x | | | | | | | | | | | | | | | | | |
| PRISTIMERIN | | | | x | | | | | | | | | | | | | | | |
| PUROMYCIN HCl | | | x | | | | | | | | | | | | | | | | |
| PURPURIN | | | | | | | | | | | | | | | x | | | | |
| PYRITHIONE ZINC | | x | | | | | | | | | | | | | | | | | |
| PYRVINIUM PAMOATE | | x | | | | | | | | | | | | | | x | | | |
| QUINACRINE HYDROCHLORIDE | | | x | | | | | | | | | | | | | | | | |
| RIBOFLAVIN | | | | | | | | | | | | | | | | x | | | |
| RIFAMPIN | | | x | | | | | | | | | | | | | | | | |
| RILUZOLE | | | | | | | | | | | | | | | | | | x | |
| ROSOLIC ACID | | | | | | | | | | | | | | | | x | | | |
| ROSUVASTATIN | | | | | | | | | x | | | | | | | x | | | |
| ROTENONE | | x | | | | | | | | | | | | | | | | | |
| RUTILANTINONE | | | | | | | | | | x | | x | | | | x | | | |
| SELAMECTIN | | | x | | | | | | | | | | | | | | | | |
| SEMUSTINE | | | | | | | | | | | | | | | x | | | | |
| SODIUM SALINOMYCIN | | | x | | | | | | | | | | | | | | | | |
| SULOCTIDIL | x | | | | | | | | | | | | | | | | | | |
| SUPROFEN METHYL ESTER | | | | | | | | | | | | | | | x | | | | |
| TANNIC ACID | | x | | | | | | | | | | | | | x | | | | |
| TEGASEROD MALEATE | | | | | | | | | | | | | | x | | | | | |
| TENIPOSIDE | | | | | | x | | | | | | | | | | | | x | |
| TETRACHLOROISOPHTHALONITRILE | | x | | | | | | | | | | | | | | | | | |
| THIMEROSAL | x | | | | | | | | | | | | | | | | | | |
| THIOTHIXENE | | | | | | | | | | | | | | | | x | | | |
| TINIDAZOLE | x | | | | | | | | | | | | | | | | | | |
| TOLNAFTATE | | | | x | | | | | | | | | | | | | | | |
| TRIFLUOPERAZINE HCl | | | | | x | | | | | | | | | | | | | | |
| TYROTHRICIN | x | | | | | | | | | | | | | | | | | | |
| USNIC ACID | | x | | | | | x | | | | | | | | | | | | |
| VALDECOXIB | | | | | | | | | | | | | | | x | | | | |
| VINCAMINE | | | | | | | | | | | | | | | x | | | | |

Figure 8B

IN VITRO CELLULAR BIOASSAY FOR NEUROTOXICITY TESTING

This application is a National Stage application filed under Rule 371 based on PCT/U.S.11/31774 filed Apr. 8, 2011, which claims priority under 35 U.S.C. §119(e) to U.S. Provisional Patent Application No. 61/342,026, filed on Apr. 8, 2010. The foregoing applications are incorporated by reference herein.

This invention was made with government support under R21 NS055774 awarded by the National Institutes of Health. The government has certain rights in the invention.

FIELD OF THE INVENTION

The present invention relates generally to neurotoxicity screening methods.

BACKGROUND OF THE INVENTION

Several publications and patent documents are cited throughout the specification in order to describe the state of the art to which this invention pertains. Each of these citations is incorporated herein by reference as though set forth in full.

There is an extraordinary need for new and better neurotoxicity assays, particularly developmental neurotoxicity (DNT) assays, that can be carried out with higher speed and lower cost (Bal-Price et al. (2008) Neurotoxicol., 29:520-531). Otherwise, the important goal of testing tens of thousands of drugs and chemicals already in the environment will never be achieved (Landrigan, P. (2010). Curr. Opin. Pediatr., 22:219-225). The concern about having so many untested compounds in the environment is not just a philosophical one. Rather, there is increasing evidence that environmental factors which have changed in recent decades are responsible for some large part of the increasing rates of autism spectrum disorders (Hertz-Picciotto & Delwiche (2009) Epidemiology 20:84-90). Beyond this concern, better methods are needed for testing compounds in the drug-development pipeline for potential neurotoxicity prior to marketing. In addition, there is a compelling rationale to reduce the reliance on whole-animal testing in mammals (Flecknell, P. (2002) ALTEX 19:73-78). In particular, there is a need to greatly reduce the use of rats for neurotoxicity testing because those methods are so expensive and slow that they, in effect, serve as an obstacle to conducting neurotoxicity testing. Furthermore, neurotoxicity testing in rats does not allow for evaluation of genetic influences on sensitivity to neurotoxic compounds. The instant invention solves the above problems.

SUMMARY OF THE INVENTION

In accordance with one aspect of the instant invention, methods for determining the neurotoxicity of a compound are provided. In a particular embodiment, the method comprises culturing *Drosophila* neurons in the presence of a compound(s) and assessing at least one characteristic of the neurons; wherein a modulation of at least one characteristic of the neuron compared to *Drosophila* neurons cultured in the absence of the compound indicates that the compound is neurotoxic. In a particular embodiment, the characteristic is cell survival, neuronal body size, neuronal body shape, neurite outgrowth, neurite structure, neurite arbor shape, synapse number, and/or synapse function.

In accordance with another aspect of the instant invention, methods for identifying a genetic marker which correlates with a modulated (increased or decreased) risk for adverse effects in a subject to a compound are provided. In a particular embodiment, the method comprises culturing mutant *Drosophila* neurons in the presence of a compound(s) and assessing at least one characteristic of the mutant *Drosophila* neurons, wherein a modulation (increase or decrease) in the severity of at least one characteristic of the mutant *Drosophila* neuron compared to wild-type *Drosophila* neurons cultured with the compound indicates that the mutation in the orthologous subject gene is indicative of a modulated risk for adverse effects to the compound in a subject having said genetic marker.

In accordance with yet another embodiment, methods for determining the presence of an increased or decreased risk for adverse effects to a compound in a subject are provided. In a particular embodiment, the method comprises detecting in the subject (e.g., in the genome) the presence or absence of a genetic marker(s) identified by the methods of the instant invention.

BRIEF DESCRIPTIONS OF THE DRAWING

FIG. 1 provides phase-contrast (60×) photomicrographic images of drug-induced neurotoxic defects induced in primary neuron culture after 3 days' in vitro exposure to the drug in the culture medium. These neurons are from developing brains of fascin-deficient mutants. FIGS. 1A and 1B show images of apparent cell death at early and late stages, respectively, without elaboration of a neurite arbor. Cell death based on biochemical criteria was confirmed using commercially available fluorescent indicators (e.g., live cells use an esterase to convert a non-fluorescent substrate to a fluorescent one, whereas dead cells are permeable to a fluorescent molecule that cannot cross the cell membrane of live cells). FIGS. 1C and 1D provide images of neurons with geometric (triangular) cell bodies with a few, greatly expanded neurite extensions which may be growth cones. FIG. 1E provides an image of a triangular cell body with thin neurites punctuated by ovoid expansions. FIG. 1F provides an image of the "ruffled cell body" defect. FIG. 1G shows an image of reduced neurite outgrowth, in which the neuron has the unusual feature of being monopolar. FIGS. 1H and 1I provide images of the "beads-on-a-string" (BOS) defect wherein regularly spaced phase-dark nodules are present within neurites.

Figure 2:
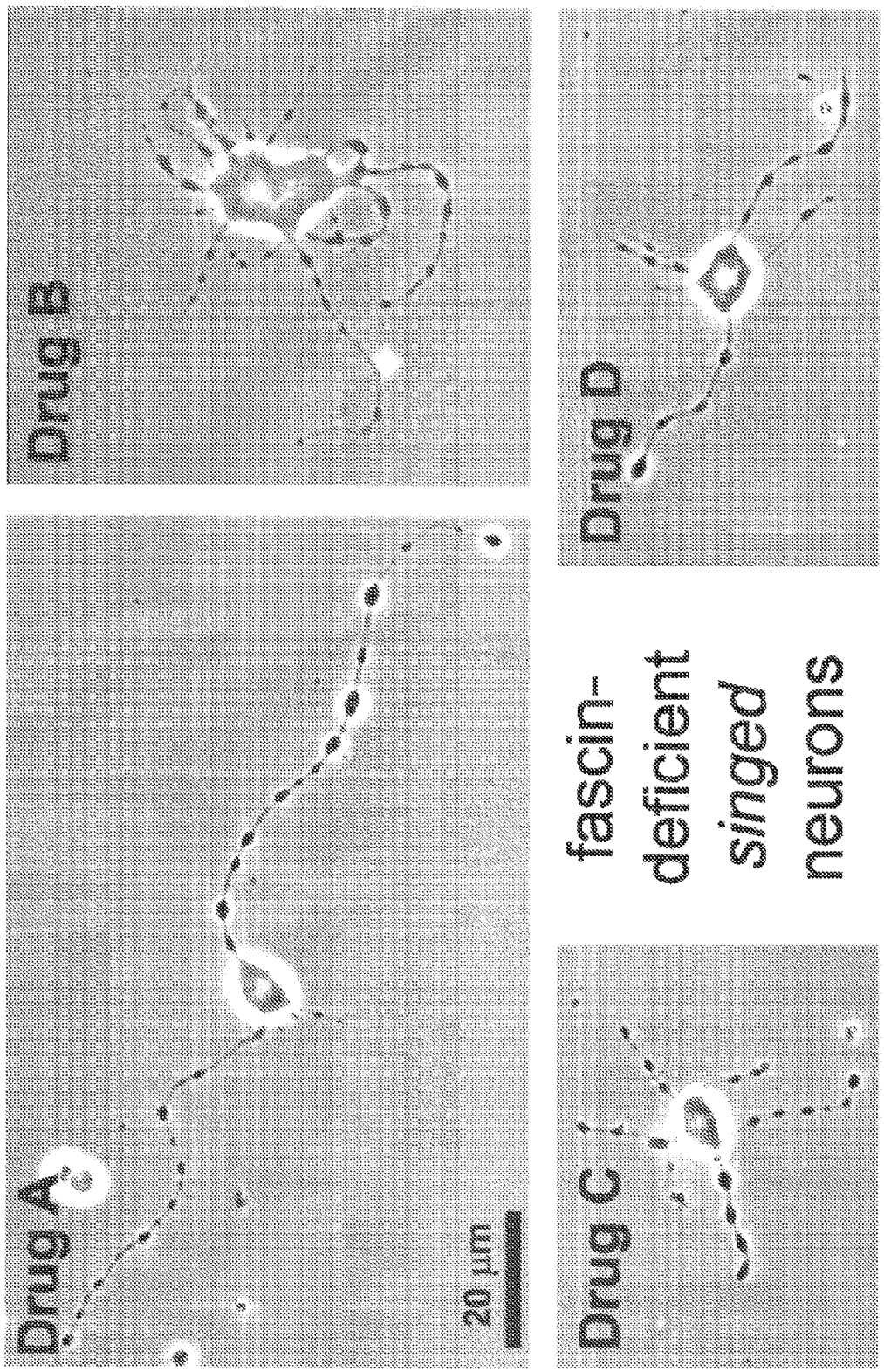

FIG. 2 provides phase-contrast images of the beads-on-a-string (BOS) defect in fascin-deficient singed (sn) mutant *Drosophila* neurons in vitro. Neurons were prepared from the larval central nervous system (CNS) and cultured for 3 days in vitro. Drugs: A—atorvastatin; B—lovastatin; C—rosuvastatin; and D—pravastatin.

FIG. 3 provides images of wild-type neurons possessing the BOS defect when cultured with a statin. Parallel cultures from the same CNS sample are shown with (right panel) or without (left panel) drug A (atorvastatin) in the culture medium. The statin effect includes inhibition of neurite outgrowth as well as intracellular beads along the neurites.

Figure 4:
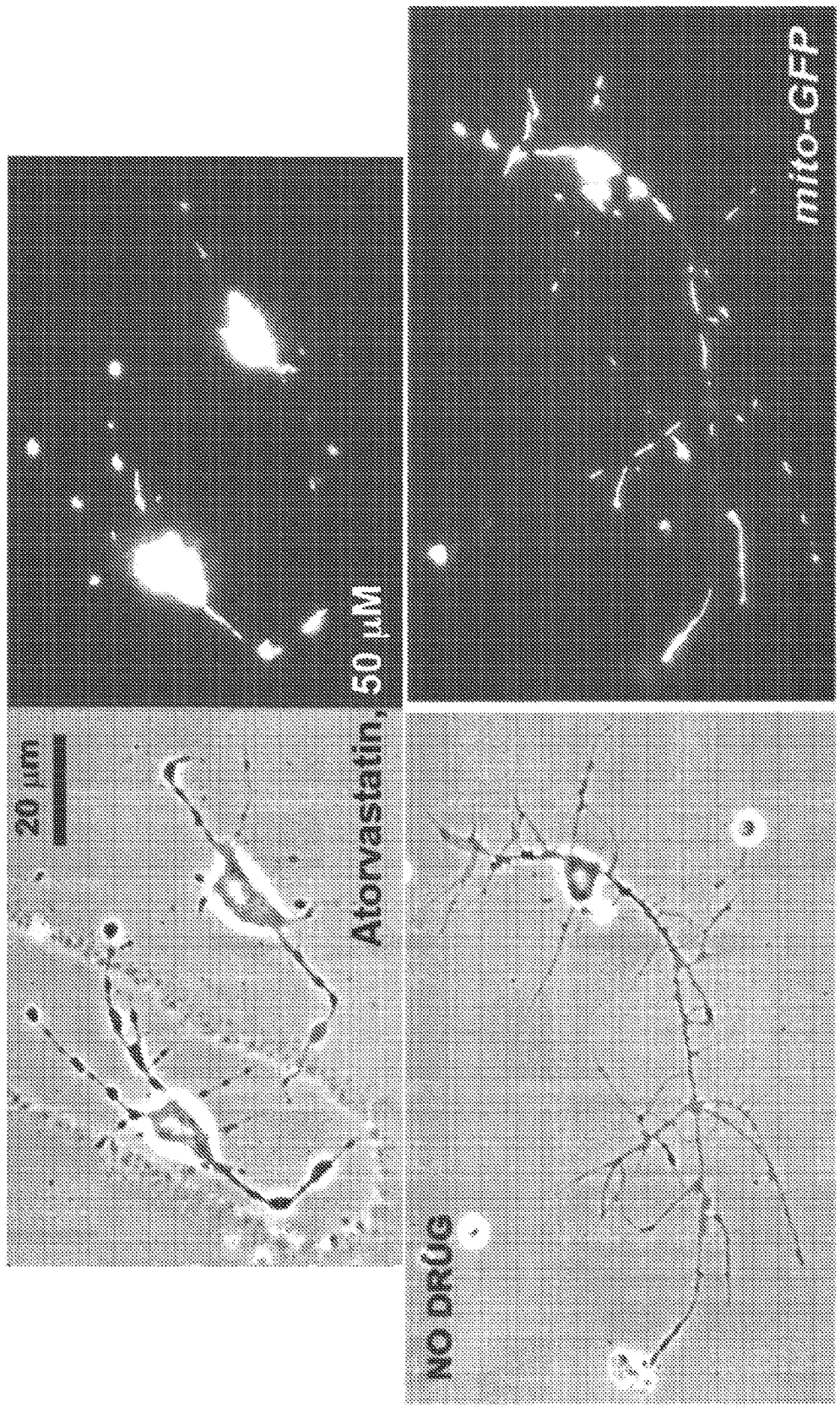

FIG. 4 provides images which demonstrate that the "beads" of the BOS defect contain aggregations of mitochondria. Phase-contrast (left) and fluorescent (right) images (60×) of wild-type neurons expressing a GFP-tagged mitochondrial protein cultured for 3 days with (top) or without (bottom) atorvastatin are provided. The genotype of the neurons is elav-Gal4/Y; UAS-mitoGFP (Pilling et al. (2006) Mol. Biol. Cell 17:2057-2068).

Figure 5:
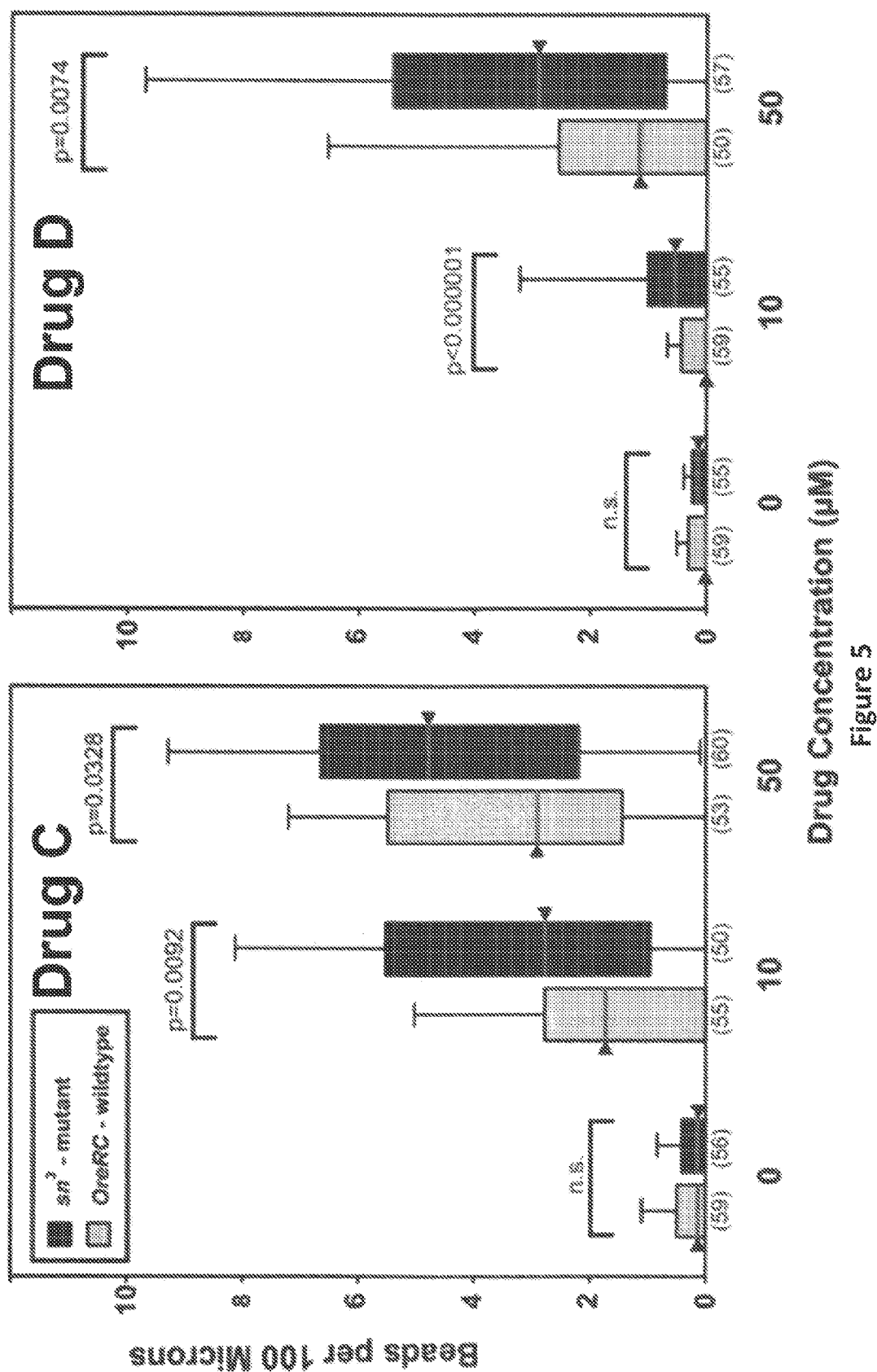

FIG. 5 shows that BOS is dose-dependent and enhanced by fascin deficiency. After 3 days in vitro, BOS was quantified in randomly selected neurons (n=# in parentheses). For each genotype, the cultures came from the same CNS. For both drugs C (rosuvastatin) and D (pravastatin), BOS density increased with dose. At each dose, the effect was enhanced in sn-mutant, fascin-deficient neurons. Box-plots show median (triangle arrow), 75th, 25th, 90th, and 10th percentiles.

Figure 6:
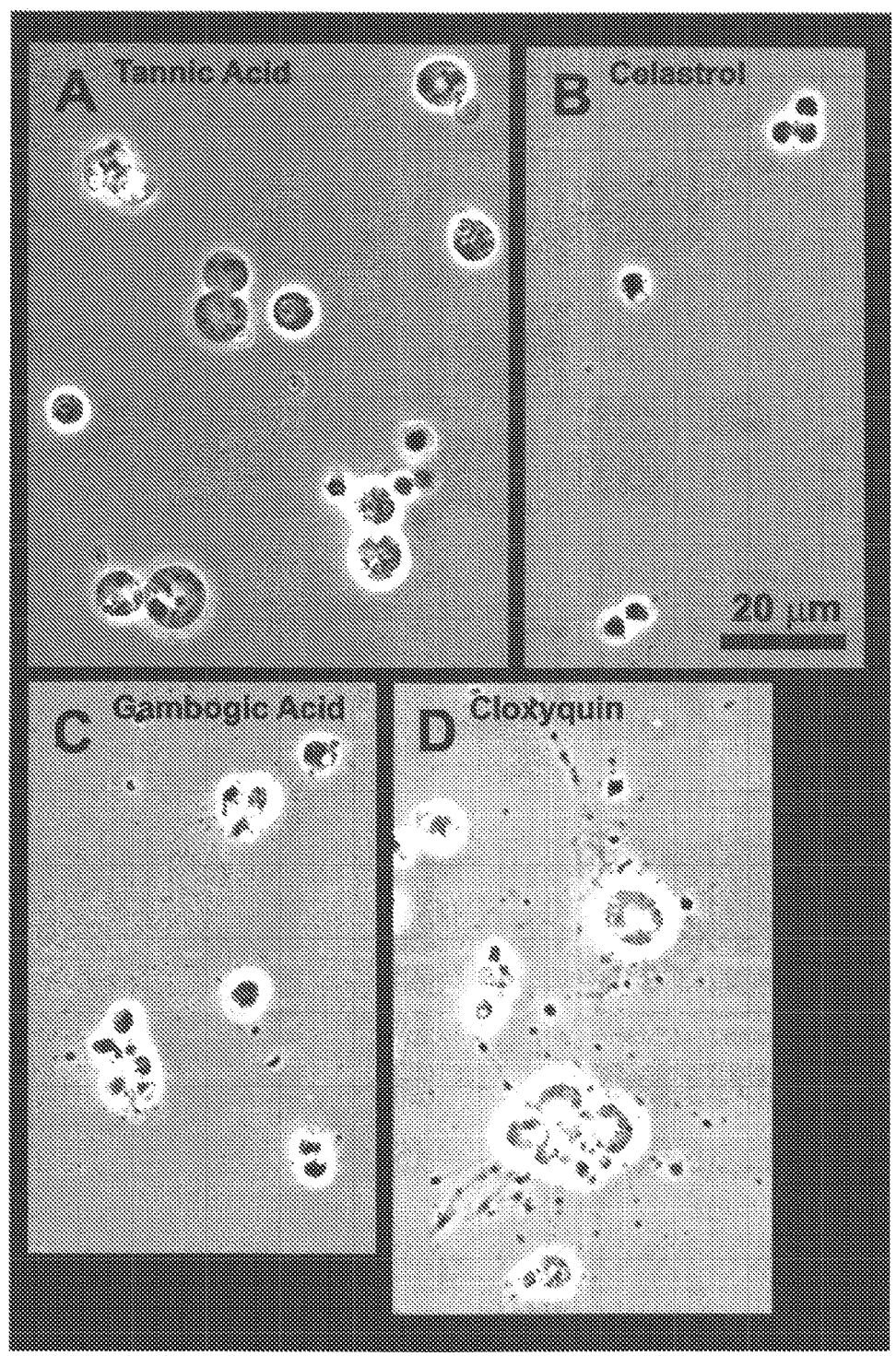

FIG. 6 provides representative images of neurotoxicity categories with apparent cell death or neurodegeneration identified by the instant screening methods. The indicated chemical name represents just one example of a compound that generated the depicted defect. The phenotype categories are: FIG. 6A: "glass marble"; FIG. 6B: "black checker"; FIG. 6C: "crumbled checker"; and FIG. 6D: "tiny bubbles".

Figure 7:
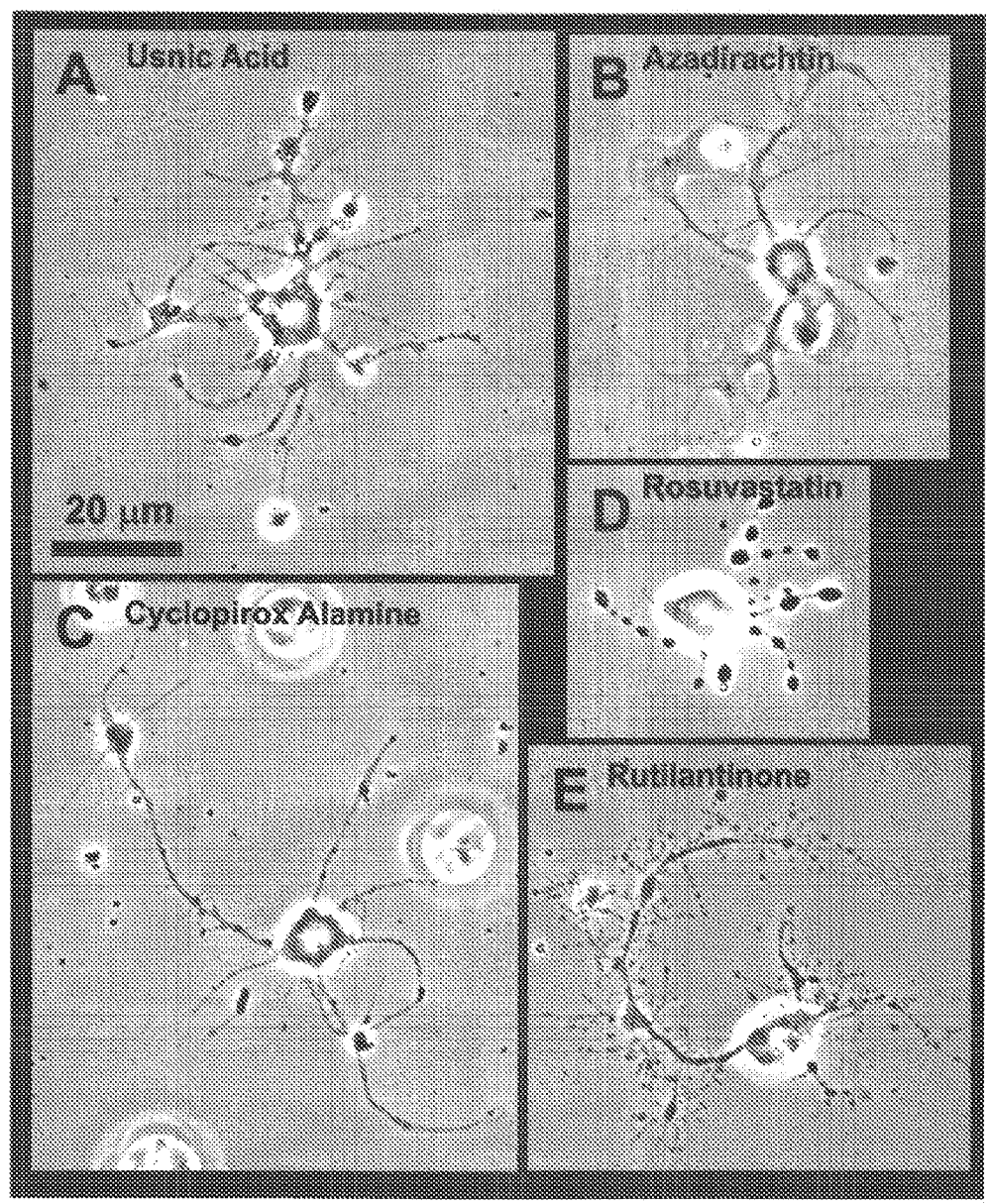
Figure 7:
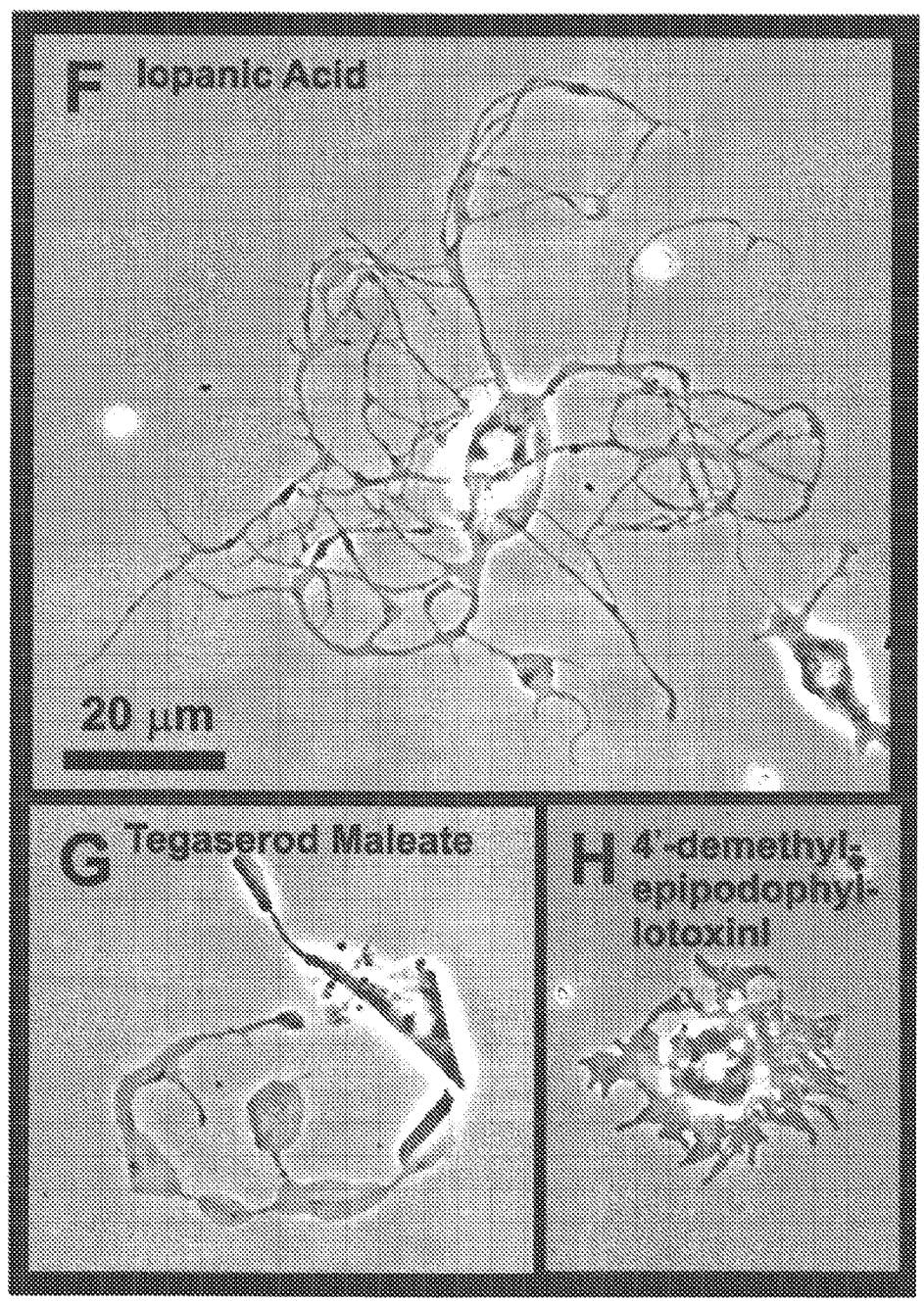
Figure 7:
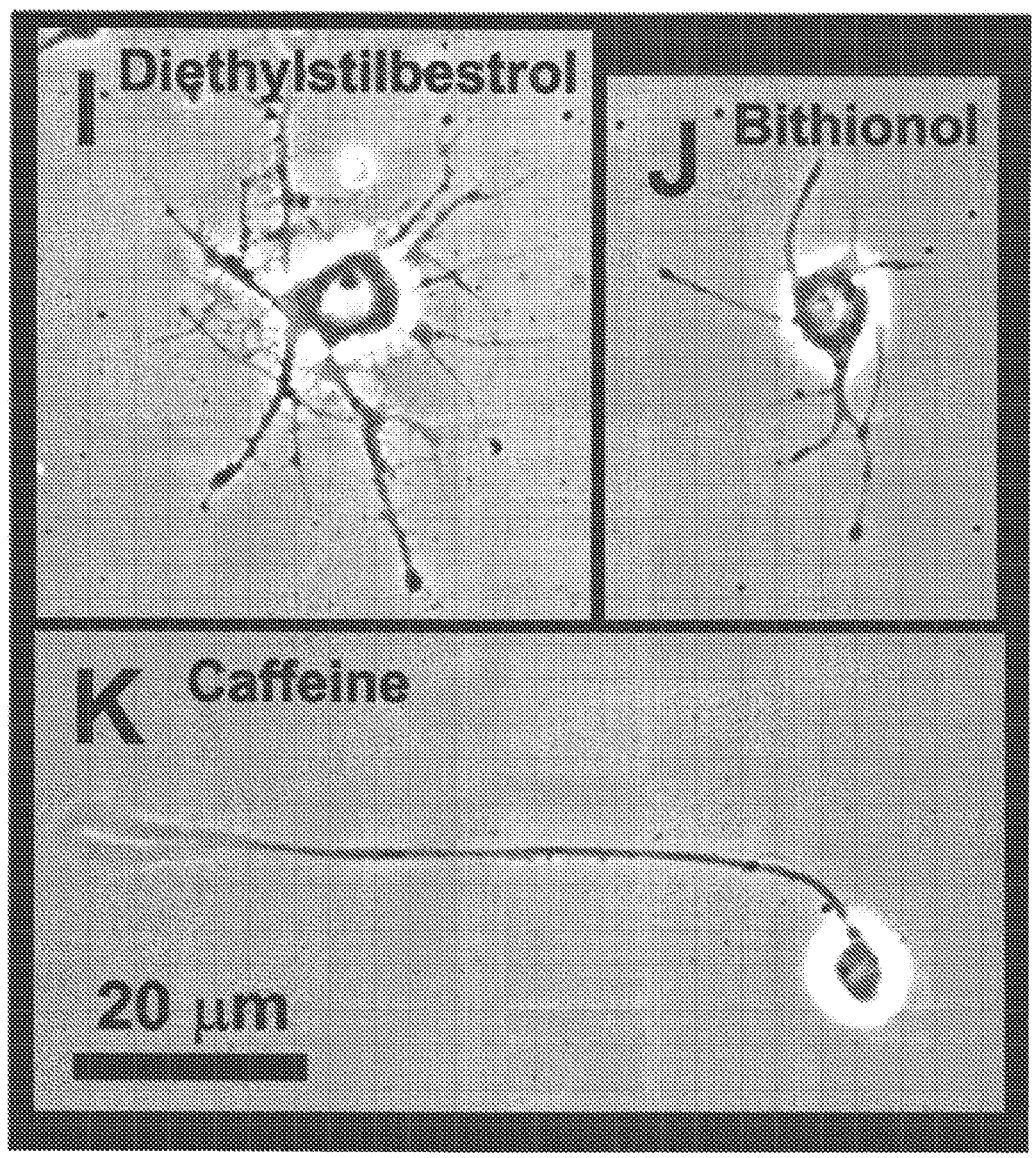

FIG. 7 provides representative images of neurotoxicity categories with abnormalities of neuronal size and/or shape, which are divided into three categories: altered neurite morphology (FIGS. 7A-7E), altered cell body shape (FIGS. 7F-7H), and reduced neurite outgrowth (FIGS. 7I-7K) identified in the instant screening methods. The indicated chemical name represents just one example of a compound that generated the depicted defect. The neurotoxic defect categories are: FIG. 7A: "multi-mini vacuoles"; FIG. 7B: "rolling stone's tongue"; FIG. 7C: "enlarged growth cone"; FIG. 7D: "beads-on-a-string"; and FIG. 7E: "beaded brush". The cell-body morphology categories are: FIG. 7F: "bloated cell body"; FIG. 7G: "geometric cell body"; and FIG. 7H: "ruffled cell". The reduced neurite outgrowth categories are: FIG. 7I: "hairy runt"; FIG. 7J: "naked runt"; and FIG. 7K: "naked monopolar".

FIGS. 8A and 8B provide a table of the all the compounds of the 1,040 screened that showed any kind of neurotoxic defect at either 10 or 50 µM. The number abbreviations for the neurotoxic defects are: 1-unclassified, 2-glass marble, 3-black checker, 4-crumbled cookie, 5-tiny bubbles, 6-multi-mini vacuoles, 7-rolling stones' tongue, 8-enlarged growth cone, 9-beads-on-a-string, 10-beaded brush, 11-vacuolated cell body, 12-bloated cell body, 13-geometric, 14-ruffled, 15-reduced arbor, 16-runt, 17-naked runt, 18-hairy runt, and 19-naked monopolar.

Figure 9:
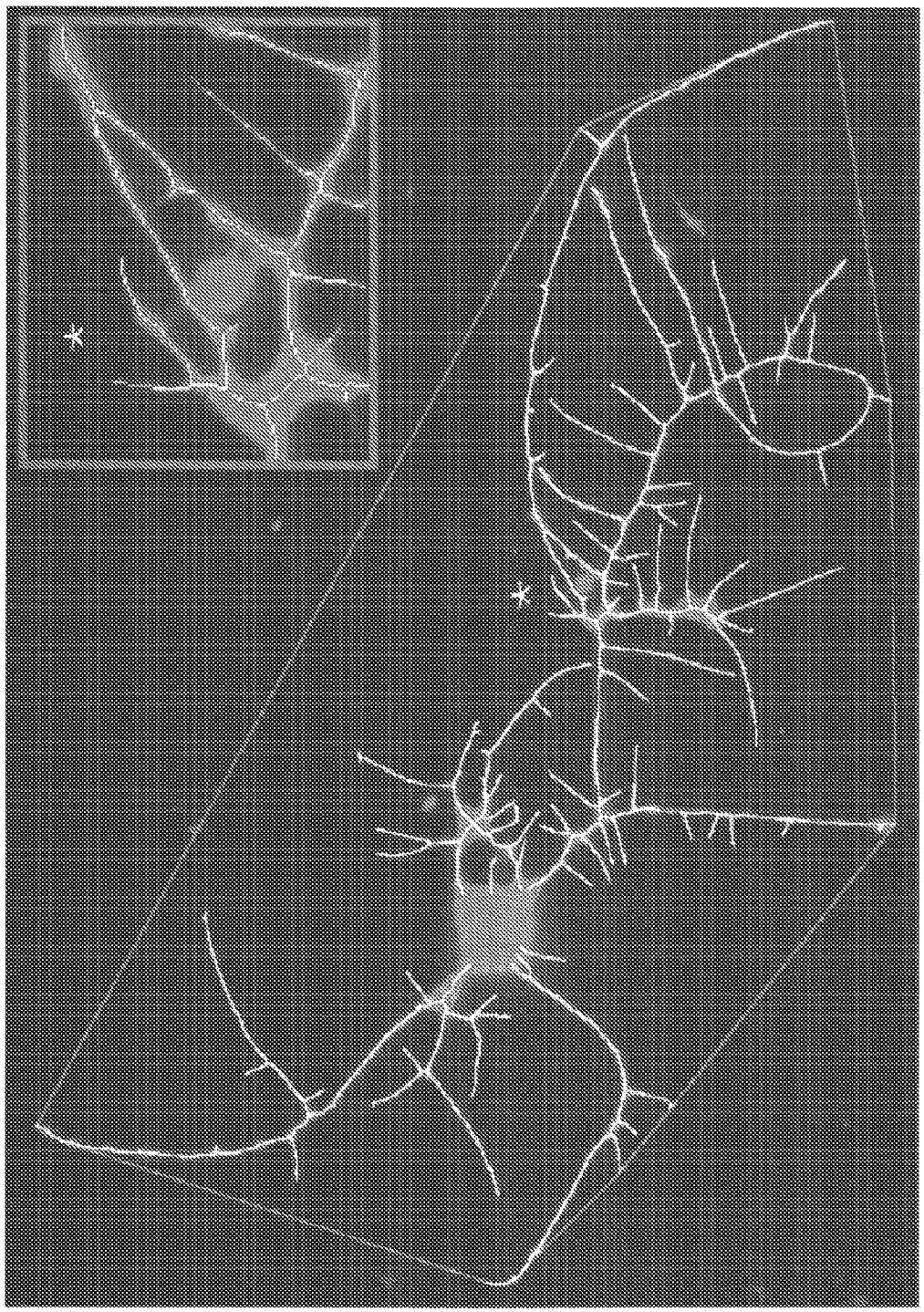

FIG. 9 provides a representative image of the output from the NeuronMetrics™ software. The skeleton has been widened to 3 pixels (except in the detail box) to allow easier visualization. Developed for the analysis of 2D images of fluorescently stained neurons, NeuronMetrics™ creates an improved (gap-free) skeleton, shown overlaid on a wild-type fluorescent-neuron image (detail in upper right), and calculates the perimeter and area of the territorial footprint (polygon, also known as neuron territory), as well as total length, a branch number estimate (corrected for neurite-neurite contacts), and Polarity Index (Narro et al. (2007) Brain Res., 1138:57-75). This neuron, from the mushroom bodies, was stained with an antibody that recognizes a neuronal membrane glycoprotein in *Drosophila*, namely Nervana 2 (Nrv2). For mushroom body neurons, the Polarity Index reflects the relative contributions of axonal neurites to the total neurite length.

DETAILED DESCRIPTION OF THE INVENTION

One strategy to achieve better neurotoxicity testing methods is to devise neurotoxicity assays based on simple model organisms (Lein et al. (2007) Environ. Health Perspect., 115: 764-768; Peterson et al. (2008) Neurotoxicol., 29:546-555). For example, the Ames test is a bacterial assay is used to predict which compounds are likely to be carcinogenic in humans (McMahon et al. (1979) Cancer Res., 39:682-693; Seifried et al. (2006) Chem. Res. Toxicol., 19:627-644). The fruit fly, *Drosophila melanogaster*, stands out among other neurotoxicity models for several reasons (Rand, M. D. (2010) Neurotoxicol. Teratol., 32:74-83). First, from a neurobehavioral standpoint, the fruit fly is the most sophisticated model organism that still offers small body and brain size, relatively simple brain architecture, short generation time, and exceptional experimental tractability due to a century of genetic methodology development. Second, there is extraordinarily good evolutionary conservation between insects and mammals of genes and genetic pathways involved in brain development and plasticity (Mayford and Kandel (1999) Trends Genet., 15:463-470). This extends to the genes whose mutations in humans cause developmental brain disorders (Inlow et al. (2004) Genetics 166:835-881; Restifo, L. L. (2005) Ment. Retard. Dev. Disabil. Res. Rev., 11:286-294; Halladay et al. (2009) Neurotoxicol., 30:811-821). Third, the available genetic tools, including both classical mutations, numerous methods for transgenic manipulation, and genomic sequence data, make the fruit fly system an ideal one in which to examine how genetic variation impacts sensitivity of both developing and mature animals to neurotoxins and neurotoxicants. This is important because data from animal models indicate that neurotoxicity sensitivity in humans is likely to vary with genetic background, just as sensitivity to certain adverse side effects due to pharmaceutical drugs can be mapped to specific genetic variants (Hornig et al. (2004) Mol. Psychiatry 9:833-845; Laviola et al. (2009) Neurosci. Biobehav. Rev., 33:560-572; Nakamura, Y. (2008) N. Engl. J. Med., 359:856-858). In other words, *Drosophila* offers the prospect of powerful Gene-X-Environment (G-X-E) interaction studies that would be impractical or impossible in model organisms higher up the evolutionary tree (zebrafish, mouse) and would be less comprehensive in simpler models like the nematode. Fourth, additional benefits for neurotoxicity testing, in scale, speed, and cellular resolution, can be achieved by use of primary dissociated culture of developing brain neurons.

In vitro neuronal culture methods, including organotypic slices, re-aggregating brain-cell cultures, primary dissociated cultures, and transformed cell lines that differentiate into neuron-like cells, show increasing promise for neurotoxicity testing (Silva et al. (2006) Toxicol. Lett., 163:1-9; Coecke et al. (2007) Environ. Health Perspect, 115:924-931; Bal-Price et al. (2008) Neurotoxicol., 29:520-531; Breier et al. (2008) Toxicol. Sci., 105:119-133; Radio et al. (2008) Neurotoxicol., 29:361-376). Each of these methods has strengths and limitations (Coecke et al. (2007) Environ. Health Perspect, 115:924-931; Bal-Price et al. (2008) Neurotoxicol., 29:520-531; LePage et al. (2005) Crit. Rev. Neurobiol., 17:27-50).

Herein, a flexible, multi-purpose cell-based neurotoxicity assays using primary dissociated neuron cultures from developing *Drosophila* brains are provided. There are at least three significant attributes that make this a very powerful approach for basic and applied neuroscience research.

First, like mammalian hippocampal neurons, neurons from the *Drosophila* mushroom bodies (an insect learning and memory brain center; Zars, T. (2000) Curr. Opin. Neurobiol., 10:790-795; Heisenberg, M. (2003) Nat. Rev. Neurosci., 4:266-275), retain biologically relevant morphogenetic features in primary dissociated culture, e.g., they extend a single axon and multiple dendrites (Kraft et al. (2006) J. Neurosci., 26:8734-8747; Kraft et al. (1998) J. Neurosci., 18:8886-8899).

Second, some single-gene mutations cause dramatic morphogenetic phenotypes of cultured neurons while the intact mutant brain is only modestly affected (Kraft et al. (2006) J. Neurosci., 26:8734-8747). Detecting these mutant phenotypes of isolated neurons in vitro opens a window to understanding gene function and can provide a starting point for drug discovery to identify potential new therapies. As described herein, the instant drug screen was used to determine whether the morphogenetic defect of fascin-deficient *Drosophila* neurons (Kraft et al. (2006) J. Neurosci., 26:8734-8747) could be rescued or enhanced by any of 1,040 known drugs. Fascin-deficient neurons have marked disruptions of the actin cytoskeleton resulting in highly abnormal neurite curvature (Kraft et al. (2006) J. Neurosci., 26:8734-8747). The instant bi-directional drug-screen takes into consideration the biological duality of fascin, a highly conserved actin-bundling protein (Edwards et al. (1995) Cell Motil. Cytoskeleton 32:1-9; Kureishy et al. (2002) Bioessays 24:350-361). On the one hand, fascin is essential for normal brain/neuronal development (Cohan et al. (2001) Cell Motil. Cytoskeleton 48:109-120; De Arcangelis et al. (2004) Gene Expr. Patterns 4:637-643; Megiorni et al. (2005) Neurosci. Lett., 381:169-174; Yamakita et al. (2009) Cell Motil. Cytoskeleton 66:524-534), whereas too much fascin in tumors promotes invasion and metastasis (Hashimoto et al. (2005) Int. J. Biochem. Cell Biol., 37:1787-1804; Chen et al. (2010) Nature 464:1062-1066). As explained herein, the instant drug screen identified several dozen drugs in each of two categories: enhancers and blockers of fascin function, for two distinct clinical indications. These results attest to the power of altered neuronal morphology detected in primary culture. In this instance, a genetically induced mutant phenotype was used and pharmacological modifiers were screened for. However, the instant screening assays may also be used with a chemically induced DNT defect prior to screening for genetic modifiers.

Third, the cultured developing *Drosophila* neurons have a striking ability to reveal morphological neurotoxic defects. As shown herein, a wide range of developmental neurotoxicity effects are detected in fascin-deficient neurons after chemical exposures in vitro (FIG. 1). The compound collection that was screened contained a majority of FDA-approved drugs, most of which are still in clinical use, and a minority of so-called "experimental" compounds used as research reagents. Some of the screened compounds that induced neurotoxic defects were known to be neurotoxic or more generally cytotoxic. For example, the anti-cancer drug paclitaxel, the protein synthesis inhibitors anisomycin and cycloheximide, and the sodium pump inhibitor ouabain all caused overt neurotoxic defects, as did the mercury-containing compound thimerosal. In other cases, e.g., the beads-on-a-string (BOS) defect which was induced solely by the four statins in the library—atorvastatin, lovastatin, rosuvastatin, and pravastatin, the striking effect of neuronal morphology had not been anticipated. These dramatic neurotoxic defects highlight the power of the instant neurotoxicity assay to reveal neurotoxicity and/or indicate its mechanism and, hence, as a "first-line" screening tool (prior to follow-up studies in mammals).

Many deleterious drug side effects are only identified after a drug is marketed and widely prescribed (Mattes et al. (2009) Clin. Pharmacol. Ther., 85:327-330). For statins, a rare drug-induced myopathy with potentially serious consequences has been associated with a single-nucleotide polymorphism (SNP) in SLCO1B1, a gene that encodes a transporter involved in hepatic uptake of statins (SEARCH Collaborative Group (2008) N. Engl. J. Med., 359:789-799). Such rare side effects may be thought of as representing G-X-E interactions, where the polymorphic variation is neutral until exposure to a particular drug. Identification of genetic risk factors for drug side effects can be translated into prevention strategies, such as using CYP2C9 polymorphisms to guide warfarin dosage for anticoagulation (Stehle et al. (2008) Clin. Pharmacokinet., 47:565-594). By analogy, neurotoxicity caused by traditional environmental toxicants may require or be modified by a G-X-E interaction, identification of which could allow vulnerable individuals to be maximally protected. Thus, drug-induced neurotoxicity can be a useful model for neurotoxicity investigation and prevention.

Herein, it is demonstrated that four different statins alter neurite-arbor morphology, reducing outgrowth and inducing the dramatic BOS defect of cultured developing brain neurons from *Drosophila* (FIG. 2). These statins differ in their potency of HMG-CoA reductase inhibition (Liao and Laufs (2005) Annu. Rev. Pharmacol. Toxicol. 45:89-118), and this correlated with their potency to induce BOS (see, e.g., FIG. 5). This is consistent with BOS resulting from HMG-CoA reductase inhibition rather than from an off-target effect. BOS was initially detected in fascin-deficient (singed-mutant) neurons, but it is also evident in wild-type neurons cultured with all four statins (e.g., FIG. 3). Statins also reduce neurite outgrowth in mammalian cultured neurons (Schulz et al. (2004) J. Neurochem., 89:24-32; Kim et al. (2009) J. Neurochem., 108:1057-1071).

BOS (FIG. 1H-1I) stood out from the other neurotoxic effects (FIG. 1A-G) because of growing evidence that some human patients taking statins suffer from significant, usually reversible, cognitive deficits or neuropsychiatric symptoms (King et al. (2003) Pharmacotherapy 23:1663-1667; Wagstaff et al. (2003) Pharmacotherapy 23:871-880; Golomb et al. (2004) Q. J. Med., 97:229-235; Galatti et al. (2006) Pharmacotherapy 26:1190-1192; Evans et al. (2009) Pharmacotherapy 29:800-811; Tatley et al. (2007) Drug Safety 30:195-201). Among community physicians, this side effect is called "statin brain". Like statin brain, BOS and the associated reduced neurite outgrowth are reversible after replacement of culture media with drug-free media. Using a transgenic GFP-tagged mitochondrial protein (Pilling et al. (2006) Mol. Biol. Cell 17:2057-2068), it was found that the beads contain aggregations of mitochondria (FIG. 4). The appearance of the beads is consistent with disrupted microtubule transport (Pilling et al. (2006) Mol. Biol. Cell 17:2057-2068), which would also explain reduced neurite outgrowth. From all the available data, statins can reversibly impair neuronal structure and function, thereby contributing to cognitive dysfunction in adult patients. Significantly, the instant invention allows for the determination of what genetic factors predispose patients to statin-induced cognitive or neuropsychiatric symptoms.

The urgency to pursue this research is enhanced by the desire of drug companies to allow use of statins in children with high cholesterol (de Ferranti et al. (2008) N. Engl. J. Med., 359:1309-1312) and the expanded indication of statins for people with normal serum cholesterol (Singh et al. (2008) Drugs Today, 44:455-471). Inhibition of HMG-CoA reductase blocks not only cholesterol biosynthesis but also the synthesis of isoprenoids that serve as essential membrane anchors for small G proteins such as Ras, Rho, and Rac (Wang et al. (2008) Trends Mol. Med., 14:37-44; Kim et al. (2009) J. Neurochem., 108:1057-1071). Mammalian neuronal culture data demonstrate that statin-induced dendritic outgrowth reduction is mediated by blockade of the isoprenoid pathway (Schulz et al. (2004) J. Neurochem., 89:24-32) and, in the case of sympathetic neurons, specifically by inhibiting RhoA activation (Kim et al. (2009) J. Neurochem., 108:1057-1071). These GTPases have critical roles in brain development and plasticity (Luo, L. (2000) Nat. Rev. Neurosci., 1:173-180; Kennedy et al. (2005) Nat. Rev. Neurosci., 6:423-434), in particular by regulation of the actin cytoskeleton (Meyer et al. (2002) J. Neurochem., 83:490-503). Moreover, mental retardation results from human gene mutations disrupting G-protein signaling (van Galen et al. (2005) Prog. Brain Res., 147:295-317). Given the sensitivity of the developing brain to toxins (Bondy et al. (2005) J. Neurosci. Res., 81:605-612), children will be at high risk for statin-induced neurotoxicity, with more widespread and more severe consequences than the rare, reversible cognitive deficits in adults. Children and adults with sequence variants in genes regulating the actin cytoskeleton will also be at particularly high risk for statin-induced neurotoxicity.

As stated herein, genetic mutations within neurons may lead to modulation of neuron sensitivity (e.g., increased or reduced) to a tested compound. For example, mutations affecting the actin cytoskeleton may enhance the vulnerability of developing neurons to statin-induced BOS defect. In particular, Inlow et al. (Genetics (2004) 166:835-881) describe seven genes which encode actin-cytoskeleton regulators and whose human orthologs cause mental retardation (MR) when mutated. Thus, the human genes are essential for brain development and cognitive function. This indicates that if allele-specific changes (allelic variants) in these genes, including but not limited to the existing loss-of-function and/or gain-of-function, alter the sensitivity of neurons (e.g., fly neurons) to statins, then polymorphisms in the corresponding human genes will be functionally relevant to the statin-induced side effects.

Four of the seven genes encode regulators or mediators of GTPase cycling and, when mutated, their human counterparts cause non-syndromic MR, i.e., MR with normal brain histology and no other phenotypes (Inlow et al. (2004) Genetics 166:835-881; van Galen et al. (2005) Prog. Brain Res., 147: 295-317). *Drosophila* rtGEF (PubMed Gene ID: 35306; e.g., GenBank Accession Nos. NM_057826.4 and NP_477174.1) encodes a Rho guanine nucleotide exchange factor; the human homolog is ARHGEF6 (PubMed Gene ID: 9459; GenBank Accession Nos. NM_004840.2 and NP_004831.1). GDP dissociation inhibitor (PubMed Gene ID: 34264; e.g., GenBank Accession Nos. NM_078800.2 and NP_523524.2) is the fly ortholog of human GDI1 (PubMed Gene ID: 2664; e.g., GenBank Accession Nos. NM_001493.2 and NP_001484.1). *Drosophila* Graf (PubMed Gene ID: 32522; e.g., GenBank Accession Nos. NM_206722.1 and NP_996445.1) is the ortholog of human OPHN1 (PubMed Gene ID: 4983; e.g., GenBank Accession Nos. NM_002547.2 and NP_002538.1); both encode GTPase activating proteins. *Drosophila* Pak (p21-activated protein kinase; PubMed Gene ID: 44039; e.g., e.g., GenBank Accession Nos. NM_169137.1 and NP_731074.1) is a downstream effector of the Rho GTPase cycle; its human ortholog is PAK3 (PubMed Gene ID: 5063; e.g., GenBank Accession Nos. NM_001128166.1 and NP_001121638.1).

The other three genes encode proteins in closer proximity to the actin cytoskeleton. Mutations of the human genes cause MR with neuropathological features. *Drosophila* cheerio (PubMed Gene ID: 42066; e.g., GenBank Accession Nos. NM_001202309.1 and NP_001189238.1) encodes filamin A, an actin-binding protein; mutations of FLNA (PubMed Gene ID: 2316; e.g., GenBank Accession Nos. NM_001110556.1 and NP_001104026.1), the human ortholog, cause periventricular nodular heterotopia. *Drosophila* mew (PubMed Gene ID: 32275; e.g., GenBank Accession Nos. NM_078590.2 and NP_511145.2) encodes integrin α7, a membrane protein that links the extracellular matrix to the actin cytoskeleton; mutations of human ITGA7 (PubMed Gene ID: 3679; e.g., GenBank Accession Nos. NM_001144996.1 and NP_001138468.1) cause congenital myopathy with MR. Fly dystrophin (PubMed Gene ID: 42327; e.g., GenBank Accession Nos. NM_001043263.1 and NP_001036728.1) and human DMD (Duchenne muscular dystrophy; PubMed Gene ID: 1756; GenBank Accession Nos. NM_000109.3 and NP_000100.2) genes encode a cytoplasmic protein (dystrophin) that links the actin cytoskeleton to the transmembrane dystroglycan complex in both muscle and brain tissue; mutations of human DMD are often associated with intellectual disability that may be worse than the muscle-weakness phenotype.

In addition to the above mutations affecting the actin cytoskeleton, mutations disrupting microtubule-based transport may also be studied as candidates for modulating neurotoxicity by using the instant in vitro assay. Notably, the actin cytoskeleton and microtubules interact in a coordinated manner for neuronal differentiation and plasticity (Georges et al. (2008) Mol. Neurobiol., 38:270-284). The disruption of neuronal structure and function by statins can lead to other organelles localized to the beads along with the mitochondria. This can be tested by immunostaining with a monoclonal antibody specific for *Drosophila* Golgi membranes (Stanley et al. (1997) Proc. Natl. Acad. Sci., 94:14467-14470). Additionally, both microtubule transport and G-protein signaling can be tested for reductions in gene function as enhancers of statin-induced BOS. Based on in vivo data, *Drosophila* neurons use kinesin-1 and dynein as microtubule motors for anterograde and retrograde transport, respectively (Pilling et al. (2006) Mol. Biol. Cell 17:2057-2068). Because strong mutations of genes encoding kinesin-1 and dynein cause axonal swellings in vivo that resemble BOS in vitro (Pilling et al. (2006) Mol. Biol. Cell 17:2057-2068), reducing wild-type kinesin-1 or dynein by 50% (in heterozygous null mutation/+ animals, which have no swellings but do have quantitative reductions in transport in vivo) will create a sensitized genetic background that enhances the sensitivity of cultured neurons to statin-induced BOS in vitro. For genetic manipulation of the small G proteins, the Rho family (RhoA, Rac, and Cdc42), can be tested using loss-of-function genotypes that allow survival to at least the late larval stage. Again, reducing G-protein function will enhance statin-induced BOS.

More generally, the list of candidate genes whose mutations or polymorphisms can cause altered neurotoxicity includes any gene whose mutations cause developmental brain disorders, with manifestations such as mental retardation (intellectual disability) or autism spectrum disorders, or whose allelic variants or gene dosage (copy number) modify risk of developmental brain disorders (Inlow et al. (2004) Genetics, 166: 835-881; Abrahams et al. (2010) Arch. Neurol., 67:395-399; Ropers (2010) Annu. Rev. Genomics Hum. Genet., 11:161-187). The majority of these genes have orthologs in *Drosophila* (Inlow et al. (2004) Genetics, 166: 835-881), and can be studied using the instant neurotoxicity assay. Notably, new human genes are being rapidly identified as being involved in the causation of developmental brain disorders. These newly identified genes can also be studied using the instant neurotoxicity assay. Specific examples of genes which can be studied in the instant neurotoxicity assay include, without limitation: Ube3a (PubMed Gene ID: 39266; e.g., GenBank Accession Nos. NM_140195.3 and NP_648452.1) encodes a ubiquitin protein ligase E3A that is essential for neuronal development and cognitive function and mutations in the human gene, UBE3A, cause Angelman syndrome; nejire (PubMed Gene ID: 43856; e.g., GenBank Accession Nos. NM_001201647.1 and NP_001188576.1) encodes cAMP response-element binding protein binding protein which is essential for synapse organization; mutations in the human gene, CREBBP, cause Rubinstein-Taybi syndrome; Tsc1 (PubMed Gene ID: 42862; e.g., GenBank Accession Nos. NM_058067.2 and NP_477415.1) and gigas (PubMed Gene ID: 40201; e.g., GenBank Accession Nos. NM_079453.2 and NP_524177.1), which encode orthologs of the mammalian tuberous sclerosis complex, TSC1 and TSC2; mutations of the human genes, hamartin and tuberin, respectively, cause tuberous sclerosis; neurexin (dnrx, neurexin-1) (PubMed Gene ID: 42646; e.g., GenBank Accession Nos. NM_001170216.1 and NP_001163687.1), which encodes a transmembrane molecule involved in synaptic organization; mutations of several members of the human NRXN gene family cause mental retardation and autism spectrum disorders; neuroligin (PubMed Gene ID: 33962; e.g., GenBank Accession Nos. NM_078772.2 and NP_523496.1) which encodes a transmembrane molecule believed to bind neurexin; mutations of several members of the human NLGN gene family cause mental retardation and autism spectrum disorders; discs large (dlg; PubMed Gene ID: 32083; e.g., GenBank Accession Nos. NM_206683.3 and NP_996406.1) which encodes a cytoplasmic protein essential for synapse development; mutations in the human gene DLG3 cause mental retardation; Neurexin-IV (PubMed Gene ID: 39387; e.g., GenBank Accession Nos. NM_168491.2 and NP_729787.2) which encodes a transmembrane neurexin-family member most closely related to mammalian CASPR2; mutations in the human gene, CNTNAP2, cause a mental retardation syndrome with autism; and fmr1 (PubMed Gene ID: 37528; e.g., GenBank Accession Nos. 1. NM_169324.2 and NP_731443.1) which expresses a protein required for normal neural development and is disrupted in fragile X.

As stated hereinabove, the instant invention encompasses bioassays for the assessment of neurotoxicity, including developmental neurotoxicity. In a particular embodiment, the method is for determining the neurotoxicity of a compound of interest. While the instant methods are described as determining the neurotoxicity of a compound, the instant invention encompasses determining the neurotoxicity of more than one compound (e.g., a combination of compounds administered concurrently or sequentially). In a particular embodiment, the method comprises: a) culturing neurons from an insect in the presence of the compound; and b) assessing at least one characteristic of the neurons, wherein a modulation of at least one characteristic of the neuron compared to neurons cultured in the absence of the compound indicates that the compound is neurotoxic (i.e., is a neurotoxin).

In a particular embodiment, the neurons are obtained from *Drosophila*, particularly *Drosophila melanogaster*. The neurons may be obtained from the central nervous system, particularly the brain of the developing or adult fruit fly. In a particular embodiment, the neurons are obtained from the mushroom bodies. In a particular embodiment, the neurons are mature or adult neurons. In a particular embodiment, the developmental stage is the wandering larva or earlier. In a particular embodiment, the neuron culture is a primary neuron culture (i.e., cells that are cultured directly from a subject or organism). In a particular embodiment, the neurons are obtained as described in Kraft et al. (J. Neurosci. (2006) 26:8734-8747 and Kraft et al. (J. Neurosci. (1998) 18:8886-8899.

Briefly, the whole CNS is dissected en bloc in culture medium from the living organism. The CNS or microdissected regions thereof are incubated in a saline solution containing collagenase and dispase. Following this enzymatic treatment, the tissue is washed and then mechanically triturated in culture medium to dissociate it into single cells. The cell suspension is distributed as equal aliquots into several sterile polystyrene cell culture dishes. Each dish has a central well, created by drilling a hole in the floor and attaching a glass cover slip to the bottom. The well is coated with Conconavalin A and laminin. This is the substrate upon which the neurons settle and grow. The cells are allowed to settle and adhere to the substrate, after which the dish is flooded with culture medium (to a final volume of 1 ml) to which no compound, one or more compounds, or carrier has been added. In a particular embodiment, the compound(s) are incorporated into the substrate.

As stated above, the neurons are cultured with the compound being tested. The neurons may be cultured with the compound for a sufficient length of time to allow the extension and elaboration of complex neurite arbors. In a particular embodiment, the neurons are cultured with the compound for at least about 1 hour, at least about 6 hours, at least about 12 hours, at least about 18 hours, at least about 24 hours, at least about 2 days, or at least about 3 days. In a particular embodiment, the neurons are cultured with more than one concentration (e.g., a concentration curve) of the compound being tested (e.g., in parallel cultures with cells derived from the same source).

Neuron cultures of the instant invention may be cultured at low densities to allow high-resolution analysis of individual neurite arbor size and shape. For example, a single whole-CNS preparation from a wandering larva distributed into six dishes provides such low-density cultures. By low density, it is intended that after 3-4 days of culture, the arbor of individual neurons can still be resolved. Once the density gets above a certain threshold, the branches cross over each other, may bundle with each other, and generally obscure each other. In another embodiment, the neuron cultures may also be cultured at higher densities (e.g., by distributing the cell suspension into fewer dishes) in order to examine synaptogenesis (e.g., the number of synapses formed) and/or synaptic transmission (e.g., synapse function). In this embodiment, the effect of compounds on synapse number (e.g., relative to neuron number and size) and/or synaptic connectivity would be measured.

The compound tested by the methods of the instant invention can be any compound (e.g., an isolated compound), particularly any drug (e.g., an FDA approved drug), organic molecule, or small molecule. For example, the compound may be a polypeptide, protein, peptide (e.g., neuropeptide), nucleic acid molecule (e.g., encoding a protein of interest), inhibitory nucleic acid molecule (e.g., antisense or siRNA), organic compound, inorganic compound (e.g., heavy metals, mercury, mercury containing compounds), or small molecule. In a particular embodiment, the compound is selected from those provided in FIG. 8.

In a particular embodiment of the instant invention, the methods of the instant invention may also be used to screen compounds to protect against, inhibit, or prevent the neurotoxicity of a first compound. For example, if a first compound(s) has been identified as neurotoxic and causes a modulation in a characteristic of the neurons, then a second compound(s) may be cultured with the neurons simultaneously or sequentially (before or after) to determine if the neuron defect is modulated. Amelioration or reduction of the neuron defect indicates that the second compound(s) can inhibit or prevent the neurotoxicity of the first compound(s). These assays may also be performed with the neuron mutant assays. Such assays can identify compounds which ameliorate or reduce the adverse effects observed with a particular compound(s) and a genetic signature.

Any characteristic of the neuron may be assessed or monitored in order to determine whether the compound of interest is neurotoxic. In a particular embodiment, the characteristic is selected from the group consisting of cell survival, neuronal body size, neuronal body shape, neurite outgrowth (neurite arbor size), and neurite arbor shape (e.g., curvature, smoothness of proximal-to-distal tapering, degree of branching, presence of abnormal internal structures, Polarity Index as an indicator of axon:dendrite arbor size ratio). In a particular embodiment, the neuron exhibits at least one of the characteristics provided in FIGS. 6-8, thereby indicating the compound tested is neurotoxic. For example, the neurons may exhibit at least one characteristic/defect selected from the group consisting of: "glass marble" (rounded up neuronal cell bodies tethered to the substrate by thin strands); "black checker" (small phase-dark neuronal cell bodies); "crumbled cookie" (small phase-dark cell bodies that appear broken into pieces); "tiny bubbles" (extensive degeneration of the neurite arbor and neuronal cell body); "multi mini vacuoles" (small vacuoles clustered in the cell body and in expanded regions along neurites); "rolling stone's tongue" (oversized broad primary neurite); "enlarged growth cone" (large growth cone-like structure near the end of the major primary neurite); "beads-on-a-string" (many ovoid nodules spaced along length of neurites); "beaded brush" (primary neurites with broad regions along length and many apparently degenerating secondary neurites); "vacuolated cell body" (vacuoles clustered in the cell body); "bloated cell body" (the cell body is distended); "geometric cell body" (cell body with very straight edges (e.g., thereby forming triangles, rectangles, trapezoids, etc.) and broad expansions along the neurites); "ruffled cell" (large lamellipodia-like region about the cell body was observed with or without short spiky neurites extending from the periphery); "reduced arbor (reduction in the size of the neurite arbor); "runt" (severe reduction in the size of the neurite arbor); "hairy runt" (severe reduction in the size of the neurite arbor but with many primary and secondary branches); "naked runt" (severe reduction in size of neurite arbor with greatly reduced secondary branching); and "naked monopolar" (long primary neurite with no secondary branches). In a particular embodiment, the characteristic is beads-on-a-string. The characteristic observed may change based on the amount/concentration of the compound delivered to the neurons. For example, lower doses of the compound may cause reduced neurite outgrowth while higher doses cause neuron death. Alternatively, lower doses may provide beneficial or desired effects (e.g., modification of a mutant phenotype), but higher doses may be neurotoxic. Moreover, the compounds can be delivered by any means to the neurons. For example, the compounds may simply be added in solution in the culture media. The compounds may also be incorporated into the substrate on the floor of the culture dish or delivered on a solid substrate such as on beads or nanoparticles.

To assess the characteristics of the neurons, the neurons may be visualized by microscopy, particularly optical microscopy such as phase contrast microscopy. In a particular embodiment, the neurons are labeled with an antibody that detects a membrane antigen, e.g., the neuron-specific antigen Nervana (Jan et al. (1982) Proc. Natl. Acad. Sci., 79:2700-2704; Sun et al., (1995) J. Neurochem., 65:434-443). The antibody may comprise a detectable label or may be recognized with another detectably labeled antibody or antibody-binding molecule. Detectable labels include, for example, chemiluminescent moieties, bioluminescent moieties, fluorescent moieties, radionuclides, isotopes, radisotopes, and metals. In a particular embodiment, the detectable label is fluorescent and cellular morphology is observed, for example, via fluorescence microscopy or confocal laser-scanning microscopy. In a particular embodiment, the neuron morphology is assessed or measured quantitatively. In a particular embodiment, neuron morphology (e.g., neurite arbor morphology including neurite length, etc.) is measured with image analysis software such as NeuronMetrics™ (see, e.g., FIG. 9 and Narro et al. (2007) Brain Res., 1138:57-75).

In a particular embodiment of the instant invention, the Drosophila neuron comprises a genotype with at least one mutation in at least one gene (e.g., at least one mutation is introduced into Drosophila neurons prior to the assay steps). The mutation may or may not result in a recognizable (e.g., morphological or viability) phenotype in the neurons. The mutation may be, for example, a point mutation(s) in coding or regulatory sequences, a deletion (e.g., portion of the gene or complete deletion of one or both alleles), an gene-disrupting insertion, an RNAi-expressing transgene insertion that may be constitutive or conditional (Dietzl et al. (2007) Nature, 448:151-156) or a transgene bearing a human-disease-associated allele. In a particular embodiment, acute reduction in gene function is effected in otherwise wild-type cultured neurons by RNA-interference (Sharma et al. (2007) Proc. Natl. Acad. Sci., 104:12925-12930; Bai et al. (2009) Nat. Protoc., 4:1502-1512). In a particular embodiment, the Drosophila mutation affects the fascin-coding gene singed. Singed-mutant neurons are fascin-deficient and exhibit the "filagree" phenotype. In yet another embodiment, the mutation is in a gene involved in actin cytoskeleton pathways and/or microtubule-based transport. Examples of Drosophila genes to be manipulated with well-established genetic tools are described hereinabove and include, without limitation, rtGEF, GDP dissociation inhibitor, Graf, Pak (p21-activated protein kinase), cheerio, mew, dystrophin, Ube3a, nejire, Tsc1, gigas, neurexin, neuroligin, Neurexin IV, and dlg.

In a particular embodiment, the methods of the instant invention are used to determine the ability of a compound to modulate the phenotype of a mutant Drosophila neuron. The compounds may be assayed for their ability to restore the mutant neurons to a more wild-type phenotype (i.e., correct the defective phenotype observed in the mutant neurons). Compounds identified as restoring the wild-type phenotype may be used to treat, inhibit, or prevent a disease or disorder associated with the mutation by administering the compound, optionally in a pharmaceutically acceptable carrier, to a subject in need thereof (e.g., a subject with the disease or disorder or a subject having the mutation in the gene or ortholog thereof). For example, compounds that restore the "filagree" phenotype to wild-type may be administered to patients (e.g., children, infants, toddlers, fetuses) with developmental brain disorders, including disorders that manifest with autistic features or mental retardations.

Compounds that are identified as worsening the phenotype of fascin-deficient mutant Drosophila neurons may be used as chemotherapeutic agents, particularly for carcinomas and neurological cancers such as malignant gliomas, to inhibit or prevent their invasion and metastasis. For example, the neurotoxic compounds may be used to treat, inhibit (e.g., reduce or slow the progression or formation), or prevent a cancer by administering the compound, optionally in a pharmaceutically acceptable carrier, to a subject in need thereof.

Compounds that are identified as neurotoxic to either wild-type or mutant Drosophila neurons may be tested in mammalian models, including primary neuron culture, brain-slice preparation, neurons differentiated from neural stem cells or from neural cell lines.

In accordance with the instant invention, methods for identifying a genetic marker, variation, or signature which correlates with an increased or decreased risk for adverse effects in a subject to a compound are provided. These methods can be performed generally as described hereinabove. In a particular embodiment, the method comprises a) culturing mutant Drosophila neurons in the presence of the compound, wherein the mutant *Drosophila* neurons' genotype comprises at least one gene mutation; and b) assessing at least one characteristic of the mutant *Drosophila* neurons (e.g., those selected from the group consisting of cell survival, neuronal body size, neuronal body shape, neurite outgrowth, and neurite arbor shape); wherein an increase or decrease in the severity of at least one defective characteristic of the mutant *Drosophila* neuron compared to wild-type *Drosophila* neurons cultured with the compound indicates that the gene mutation is the gene marker correlated with an increased or decreased risk for adverse effects to the compound in a subject having a mutation or allelic variant in the orthologous gene. In a particular embodiment, the tested compound is an administered drug. In another embodiment, the compound is an environmental compound that may be naturally occurring or manmade. The instant invention also encompasses methods of screening subjects for the identified genetic marker prior to administration of the compound.

Definitions

The following definitions are provided to facilitate an understanding of the present invention:

As used herein, the term "culturing" refers to growing a population of cells under suitable conditions in a liquid or solid medium. In other words, the term "culturing" refers to the in vitro differentiation and function of cells or organisms on or in an appropriate media.

The term "neurotoxin" refers to any substance (natural or artificial) that inhibits neuronal structure or function—i.e., is toxic to neurons.

As used herein, the term "small molecule" refers to a substance or compound that has a relatively low molecular weight (e.g., less than 4,000, particularly less than 2,000). Typically, small molecules are organic, but are not proteins, polypeptides, or nucleic acids, though they may be amino acids or dipeptides.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

The term "gene" refers to a nucleic acid (e.g., within the genome) comprising an open reading frame encoding a polypeptide, including both exon and (optionally) intron sequences. The nucleic acid may also optionally include non-coding sequences such as promoter or enhancer sequences that regulate the expression of the gene.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxillary agent, filler, disintegrant, lubricating agent, binder, stabilizer, preservative or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The pharmaceutical composition of the present invention can be prepared, for example, in liquid form, or can be in dried powder form (e.g., lyophilized). Suitable pharmaceutical carriers are described, for example, in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The following examples are provided to illustrate certain embodiments of the invention. They are not intended to limit the invention in any way.

EXAMPLE 1

Primary neuron cultures from developing larval central nervous systems (CNS) of *Drosophila* were prepared as described (Kraft et al. (2006) J. Neurosci., 26:8734-8747; Kraft et al. (1998) J. Neurosci., 18:8886-8899). The neurons from developing brains of normal or mutant (singed-mutant) *Drosophila melanogaster* were contacted with a compound of interest (particularly those from the National Institute of Neurological Disorders and Stroke (NINDS) Custom Collection II library) at a range of doses (e.g., 10 and 50 $\mu$M) and cultured for several days (e.g., 3 days) in vitro under standard conditions that normally allow the extension and elaboration of complex neurite arbors. Phase-contrast (60×) images of the neurons were then obtained. The neurons were then assessed on a variety of phenotypes including cell survival, alteration in neuronal cell body size or shape, neurite outgrowth (manifest by neurite arbor size), and alterations in neurite arbor size (e.g., curvature, smoothness or proximal-to-distal tapering, presence of abnormal internal structures, degree of branching). These parameters can be quantified by using fluorescent labeling methods and software.

1,040 drugs were screened for the ability to modify the "filagree" phenotype of fascin-deficient singed-mutant neurons in vitro. 48 of the tested drugs normalized the neurite arbors (restored the neurons to a more wild-type phenotype). These identified drugs could be administered to patients (e.g., children, infants) with developmental brain disorders. Twenty-one of these compounds are preferred candidates because they did not induce any neurotoxic defects at either dose. Additionally, 34 drugs were determined to intensify the filagree defect. These drugs could be administered to patients with invasive carcinomas or gliomas. Twenty-two of these are preferred candidates because they did not induce any neurotoxic defects at either dose. FIG. 1 shows a survey of the range of developmental neurotoxicity effects detected in fascin-deficient neurons after chemical exposures in vitro.

Four of the 1,040 drugs tested were statins, which are common cholesterol-lowering drugs. All 4 statins, but no other drugs, caused intra-neurite nodules (BOS) as well as reduced neurite outgrowth (FIG. 2). This effect was seen with both singed-mutant and wild-type (OreRC) neurons (FIG. 3). Statin-induced "beads" formed within 24 hours of in vitro culture. When the statin was washed out and the cells were cultured in drug-free medium, the BOS phenotype and inhibited neurite outgrowth were reversed. Notably, statins cause severe, reversible cognitive dysfunctions in small number of patients.

Using a transgenic GFP-tagged mitochondrial protein (Pilling et al. (2006) Mol. Biol. Cell 17:2057-2068), it was determined that the beads contain aggregations of mitochondria (FIG. 4). The appearance of the beads is consistent with disrupted microtubule transport (Pilling et al. (2006) Mol. Biol. Cell 17:2057-2068).

Singed mutations enhanced the sensitivity of cultured neurons to the BOS phenotype induced by rosuvastatin and pravastatin (FIG. 5). *Drosophila* genetics and neuron culture can be used to identify genetic variation that puts humans at risk for statin-induced cognitive defects. Human FSCN1, the ortholog of *Drosophila* singed, is polymorphic, with seven SNPs whose frequencies have been determined in four distinct human populations. These SNPs, as well as other yet-unknown allelic variants in human FSCN1, are candidate markers for enhanced sensitivity to statin-induced neurotoxicity.

In another experiment, testing cultured neurons with mutations in the *Drosophila* fragile X mental retardation 1 gene (dfmr1; the ortholog of human FMR1, mutations of which cause fragile X syndrome), pravastatin induced a less severe BOS defect than it did in control neurons. In this case, the genetic control was designed (Michel et al. (2004). J. Neurosci., 23:5798-5809) to be identical in every possible way, except for the presence or absence of a normal dfmr1 gene. Hence, these results strongly indicate that the gene whose human ortholog is responsible for the most common hereditary mental retardation disorder regulates the sensitivity of neurons to statin-induced neurotoxicity.

FIGS. 6 and 7 provide images of the neurotoxic defects observed in the screening methods, providing specific examples of the categories used to classify compounds. FIG. 8 also summarizes the neurotoxic effects observed and identifies which drugs caused them in table format. Many compounds (79) induce apparent cell death either at both doses (10 and 50 μM) or at the high dose only (50 μM). For the vast majority of such drugs, neurons died without extending neurites (FIGS. 6A-C). Rarely, a drug caused degeneration after extension of a neurite arbor (FIG. 6D). Four distinctive categories were observed (in descending order of frequency): FIG. 6A—"Glass Marble": rounded up neuronal cell bodies tethered to the substrate by thin strands; FIG. 6B—"Black Checker": small phase-dark neuronal cell bodies; FIG. 6C—"Crumbled Cookie": small phase-dark cell bodies that appear broken into pieces; FIG. 6D—"Tiny Bubbles": extensive degeneration of the neurite arbor and neuronal cell body.

FIGS. 7A-7E show images of phenotypes with altered neurite morphology. 2 drugs yielded "multi mini vacuoles" characterized by small vacuoles clustered in the cell body and in expanded regions along neurites (FIG. 7A). One drug caused "Rolling Stone's tongue" characterized by oversized broad primary neurite (FIG. 7B). One drug also caused the "enlarged growth cone" phenotype characterized by a large growth cone-like structure near the end of the major primary neurite (FIG. 7C). FIG. 7D depicts the "beads-on-a-string" defect caused by 4 drugs and characterized by many ovoid nodules spaced along the length of neurites. Three drugs caused the "beaded brush" phenotype characterized by primary neurites with broad regions along length and many apparently degenerating secondary neurites.

FIGS. 7F-7H show images of compound induced defects with altered cell body shape. Three drugs caused the "bloated cell body" phenotype wherein the cell body distended. Four drugs caused the "geometric cell body" phenotype characterized by a triangular, trapezoidal, or rectangular-shaped cell body in which the usually curvilinear contour of the cell body is replaced with straight sides. The "ruffled cell body" phenotype was observed with three drugs wherein a large, irregular lamellipodia-like region about the cell body was observed with or without short spiky neurites extending from the periphery.

FIGS. 7I-7K show images of compound-induced defects with reduced neurite outgrowth. Neurite arbor size was reduced by 71 compounds. The three extreme classes are shown in FIGS. 7I-7K. Six compounds yielded the "hairy runt" defect wherein there is a severe reduction in the size of the neurite arbor but with many primary and secondary branches. Ten compounds cause the "naked runt" defect characterized by severe reduction in size of neurite arbor with greatly reduced secondary branching. One compound caused the "naked monopolar" phenotype characterized by a long primary neurite with no secondary branches.

EXAMPLE 2

The gene-X-environment (G-X-E) interaction (e.g., wherein mutations affecting the actin cytoskeleton enhance the vulnerability of developing fruit fly brain neurons to the statin-induced BOS defect) may be tested. Notably, HMG-CoA reductase-dependent isoprenylation and G-protein signaling regulates the actin cytoskeleton. Also as demonstrated above, a loss-of-function mutation in the fruit fly fascin gene (singed, sn) enhances the sensitivity to statin-induced BOS in vitro (FIG. 5). While fruit flies can not synthesize cholesterol, it is an essential nutrient. Moreover, HMGCoA reductase is highly conserved in *Drosophila*, as it is regulated by AMPK which is necessary for neuronal health (Tschäpe et al. (2002) EMBO J., 21:6367-6376). Therefore, statin effects on other pathways in neurons independent of its effects on cholesterol biosynthesis may be studied.

Using techniques previously described (Kraft et al. (2006) J. Neurosci., 26:8734-8747; Kraft et al. (1998) J. Neurosci., 18:8886-8899), primary neuron cultures will be prepared from developing larval CNS of *Drosophila* mutants and their most appropriate genetic controls. For each gene, one or more loss-of function alleles will be tested. Neurons dissociated from a single CNS can be split into six cultures, allowing two genotypes to be tested in parallel at each of various (e.g., three) drug concentrations (e.g., 0, 10, and 50 μM). One high- and one low-potency statin (as in FIG. 5) may then be tested. After culturing (e.g., for about 3 days) in vitro, neurons (e.g., about 50-60) will be selected at random from each dish for image-acquisition by phase-contrast microscopy, which provides the best data for bead counting. Each culture dish may have a gridded-coverslip floor that allows the "address" of imaged neurons to be recorded so that they can be found later, e.g., after immunostaining. Neurons may also be fixed and labeled with an antibody that detects a membrane antigen, providing a strong, uniform signal throughout the neurite arbor. Neurons previously selected may also be re-imaged by fluorescence microscopy and analyzed using NeuronMetrics™ software (see, e.g., FIG. 9; (Narro et al. (2007) Brain Res., 1138:57-75). NeuronMetrics™ numerical output includes total neurite length, which may be used to calculate number of beads per 100 μm. Statistical comparisons between genotypes will be made, e.g., using the Mann-Whitney Rank-Sum test (FIG. 5). Mutations will alter both statin-induced BOS and reduced neurite outgrowth in a parallel manner. To confirm this, the experiments may be repeated using genetically marked mushroom body gamma neurons whose size and shape distributions characterized previously (Kraft et al. (2006) J. Neurosci., 26:8734-8747; Kraft et al. (1998) J. Neurosci., 18:8886-8899).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for determining the neurotoxicity of a compound comprising
    a) culturing *Drosophila* neurons in the presence of said compound; and
    b) assessing at least one characteristic of the neurons selected from the group of characteristics consisting of cell survival, neuronal body size, neuronal body shape, neurite outgrowth, neurite structure, neurite arbor shape, synapse number, and synapse function;
    wherein a modulation of at least one characteristic of the neuron compared to *Drosophila* neurons cultured in the absence of the compound indicates that said compound is neurotoxic.

2. The method of claim 1, wherein said *Drosophila* neurons are obtained from all or part of the central nervous system of *Drosophila*.

3. The method of claim 2, wherein the *Drosophila* expresses at least one marker for the identification of a neuronal subtype.

4. The method of claim 3, wherein said neuronal subtype is a mushroom body neuron.

5. The method of claim 1, wherein said *Drosophila* neurons are obtained from *Drosophila* wandering larva or an earlier developmental stage.

6. The method of claim 1, wherein step b) comprises observing said *Drosophila* neurons by optical microscopy.

7. The method of claim 1, further comprising immunostaining said *Drosophila* neurons with antibodies immunologically specific for a neuron membrane antigen.

8. The method of claim 1, wherein said *Drosophila* neurons are mutant *Drosophila* neurons comprising at least one mutation in at least one gene.

9. The method of claim 8, wherein said gene is selected from the group consisting of singed, rho-type guanine exchange factor (rtGEF), GDP dissociation inhibitor, Graf, p21-activated protein kinase (Pak), cheerio, mew, dystrophin, ubiquitin protein ligase E3A (Ube3a), nejire, tuberous sclerosis complex 1 (Tsc1), gigas, neurexin, neuroligin, Neurexin IV, and discs large (dlg).

10. The method of claim 8, wherein said mutation causes an intellectual disability.

11. The method of claim 1, wherein said compound is a HMG CoA reductase inhibitor.

12. The method of claim 11, wherein step b) comprises assessing the neurons for a beads-on-a-string phenotype, wherein said beads-on-a-string phenotype comprises ovoid nodules spaced along the length of a neurite.

13. The method of claim 1, wherein step b) comprises quantitating characteristics of the neurons with imaging software.

14. The method of claim 1, wherein a reduction in neurite outgrowth compared to *Drosophila* neurons cultured in the absence of the compound indicates that said compound is neurotoxic.

15. The method of claim 1, wherein step b) comprises assessing the neurons for a beads-on-a-string phenotype, wherein said beads-on-a-string phenotype comprises ovoid nodules spaced along the length of a neurite.

16. The method of claim 1, wherein step a) comprises culturing *Drosophila* neurons in the presence of more than one concentration of said compound.

17. The method of claim 16, wherein step a) comprises culturing *Drosophila* neurons in the presence of a concentration curve of said compound.

* * * * *